United States Patent
Liu et al.

(10) Patent No.: US 7,098,332 B2
(45) Date of Patent: Aug. 29, 2006

(54) 5,8-DIHYDRO-6H-PYRIDO [2,3-D]PYRIMIDIN-7-ONES

(75) Inventors: Jin-Jun Liu, Warren, NJ (US); Kin-Chun Luk, North Caldwell, NJ (US)

(73) Assignee: Hoffmann-La Roche Inc., Nutley, NJ (US)

( * ) Notice: Subject to any disclaimer, the term of this patent is extended or adjusted under 35 U.S.C. 154(b) by 245 days.

(21) Appl. No.: 10/731,594

(22) Filed: Dec. 8, 2003

(65) Prior Publication Data

US 2004/0122029 A1    Jun. 24, 2004

Related U.S. Application Data

(60) Provisional application No. 60/434,969, filed on Dec. 20, 2002, provisional application No. 60/513,615, filed on Oct. 23, 2003.

(51) Int. Cl.
C07D 471/04    (2006.01)
A61K 31/519    (2006.01)

(52) U.S. Cl. .................... 544/279; 514/264.11
(58) Field of Classification Search ................ 544/279; 514/264.11
See application file for complete search history.

(56) References Cited

U.S. PATENT DOCUMENTS 6,150,373 A    11/2000    Harris et al.

2004/0043388 A1 *    3/2004    Come et al. .................... 435/6

FOREIGN PATENT DOCUMENTS

| WO | WO 96/34867 | 11/1996 |
|---|---|---|
| WO | WO 98/24432 | 6/1998 |
| WO | WO 98/33798 | 8/1998 |
| WO | WO 00/55148 | 9/2000 |
| WO | WO 01/64679 | 9/2001 |
| WO | WO 02/12237 | 2/2002 |
| WO | WO 02/12238 | 2/2002 |
| WO | WO 02/18380 | 3/2002 |

* cited by examiner

*Primary Examiner*—Thomas C. McKenzie
(74) *Attorney, Agent, or Firm*—George W. Johnston; Patricia S. Rocha-Tramaloni; David E. Wildman

(57) ABSTRACT

The invention provides 5,8-dihydro-6H-pyrido[2,3-d]pyrimidin-7-one compounds that are selective inhibitors of KDR and FGFR kinases, and are useful in the treatment of cancers. The compounds have the generic structure I

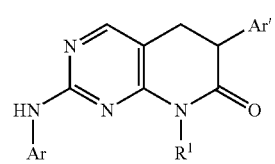

where Ar, Ar', and $R^1$ are as set forth in the present specification. The invention also provides pharmaceutical compositions containing these compounds and methods for their use.

21 Claims, No Drawings

5,8-DIHYDRO-6H-PYRIDO [2,3-D]PYRIMIDIN-7-ONES

PRIORITY TO PROVISIONAL APPLICATION(S) UNDER 35 U.S.C. §119(e)

This application claims priority under 35 U.S.C. §119(e) of provisional applications(s) Ser. No. 60/434,969, filed on Dec. 20, 2002 and Ser. No. 60/513,615, filed on Oct. 23, 2003.

FIELD OF THE INVENTION

The present invention is directed to novel dihydropyridinone compounds that inhibit KDR (kinase insert domain-containing receptor) and FGFR (fibroblast growth factor receptor) kinases. These compounds and their pharmaceutically acceptable salts have antiproliferative activity and are useful in the treatment or control of cancer, in particular solid tumors. In addition these compounds have advantageous bioavailability profiles. This invention is also directed to pharmaceutical compositions containing such compounds and to methods of treating or controlling cancer, most particularly the treatment or control of breast, lung, colon and prostate tumors.

BACKGROUND OF THE INVENTION

Protein kinases are a class of proteins (enzymes) that regulate a variety of cellular functions. This is accomplished by the phosphorylation of specific amino acids on protein substrates resulting in conformational alteration of the substrate protein. The conformational change modulates the activity of the substrate or its ability to interact with other binding partners. The enzyme activity of the protein kinase refers to the rate at which the kinase adds phosphate groups to a substrate. It can be measured, for example, by determining the amount of a substrate that is converted to a product as a function of time. Phosphorylation of a substrate occurs at the active-site of a protein kinase.

Tyrosine kinases are a subset of protein kinases that catalyze the transfer of the terminal phosphate of adenosine triphosphate (ATP) to tyrosine residues on protein substrates. These kinases play an important part in the propagation of growth factor signal transduction that leads to cellular proliferation, differentiation and migration.

For example, fibroblast growth factor (FGF) and vascular endothelial growth factor (VEGF) have been recognized as important mediators of tumor promoted angiogenesis. VEGF activates endothelial cells by signaling through two high affinity receptors, one of which is the kinase insert domain-containing receptor (KDR). See, Hennequin L. F. et. al., J. Med. Chem. 2002, 45(6), pp 1300. FGF activates endothelial cells by signaling through the FGF receptor (FGFR). Solid tumors depend upon the formation of new blood vessels (angiogenesis) to grow. Accordingly, inhibitors of the receptors FGFR and KDR that interfere with the growth signal transduction, and thus slow down or prevent angiogenesis, are useful agents in the prevention and treatment of solid tumors. See, Klohs W. E. et. al., Current Opinion in Biotechnology 1999, 10, p. 544.

There are several examples of small molecule inhibitors of protein kinase catalytic activity. In particular, small molecule inhibitors typically block the phosphorylation of substrates by tightly interacting with the protein kinase ATP binding site (or "active site"). See, WO 98/24432 and Hennequin L. F. et. al., J. Med. Chem. 2002, 45(6), pp 1300.

Several of these compounds inhibit multiple targets. For example, WO 99/61444 (Warner-Lambert) discloses bicyclic pyrimidines and bicyclic 3,4-dihydropyrimidines of formula

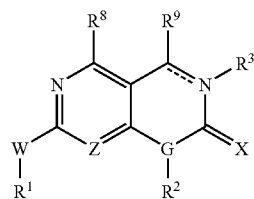

that are asserted to inhibit cyclin dependent kinases Cdk1, Cdk2 and Cdk4 as well as the growth factor receptor tyrosine kinase enzymes PDGFR and FGFR. Some compounds are also asserted to inhibit Cdk6.

WO 01/55148A1 discloses a method for treating neurodegenerative diseases in mammals comprising administering an effective amount of a cyclin-dependent kinase inhibitors, preferably using Cdk inhibitors of formula

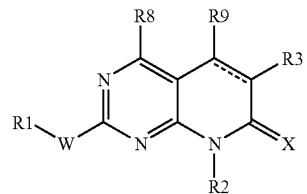

U.S. Pat. No. 6,150,373 discloses bicyclic nitrogen heterocycles of formula

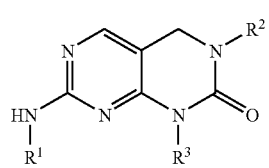

that are stated to inhibit the T-cell tyrosine kinase p56$^{lck}$.

WO 02/18380 A1 discloses 7-oxo pyridopyrimidines of formula

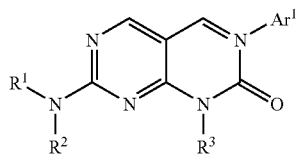

that are stated to inhibit p38 mediated cellular functions and are thus inhibitors of cellular proliferation.

WO 96/34867 discloses 6-aryl pyrido[2,3-d]pyrimidine 7-imines, 7-ones, and 7-thiones of formula

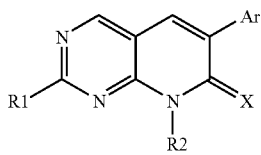

are inhibitors of protein kinases, and useful in treating cellular proliferation mediated diseases.

WO 98/33798 discloses pyrido[2,3-d]pyrimidines and 4-aminopyrimidines as inhibitors of cellular proliferation. Specifically, this publication discloses a group of 7,8-dihydro-2-(amino and thio)pyrido[2,3-d]pyrimidines and 2,4-diaminopyrimidines that are potent inhibitors of cyclin-dependent kinases (Cdks) and growth mediated kinases.

WO 01/64679 A1 discloses 1,5-disubstituted-3,4-dihydro-1H-pyrimido[4,5-D]pyrimidin-2-one compounds of formula

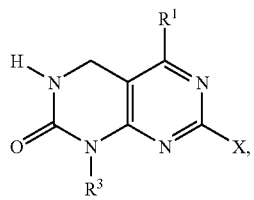 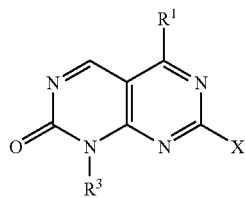

that are stated to be useful in treating CSBP/P38 kinase mediated diseases.

WO 02/12237 A2 discloses a process for preparing 2-(4-pyridyl)amino-6-dialkoxyphenyl-pyrido[2,3-d]pyrimidin-7-ones, and WO 02/12238 A2 discloses 2-(4-pyridyl)amino-6-dialkoxyphenyl-pyrido[2,3-d]pyrimidin-7-ones of formula (I).

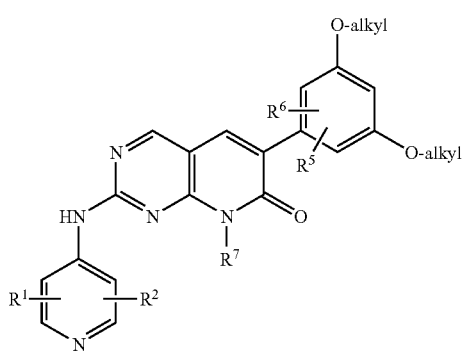

These compounds are asserted to be useful in treating diseases resulting from uncontrolled cell growth.

There continues to be a need for easily synthesized, small-molecule compounds effective in inhibiting the catalytic activity of protein kinases, in particular FGFR and KDR kinases for treating one or more types of solid tumors. It is particularly desirable to provide small molecule inhibitors that are selective for FGFR and KDR. This is desirable because the potential concomitant inhibition of targets involved in angiogenesis could provide better efficacy. On the other hand, toxicity and other undesirable complications may follow from inhibiting multiple targets. It is preferable that such small molecule inhibitors also possess advantageous bioavailability profiles. It is therefore desirable to provide such compounds and pharmaceutical compositions containing these compounds.

SUMMARY OF THE INVENTION

The present invention relates to novel dihydropyridinone compounds capable of selectively inhibiting the activity of KDR and FGFR. These compounds are useful for the treatment or control of cancer, in particular the treatment or control of solid tumors. In particular this invention relates to compounds of formulas I and II:

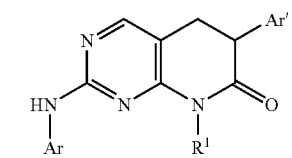

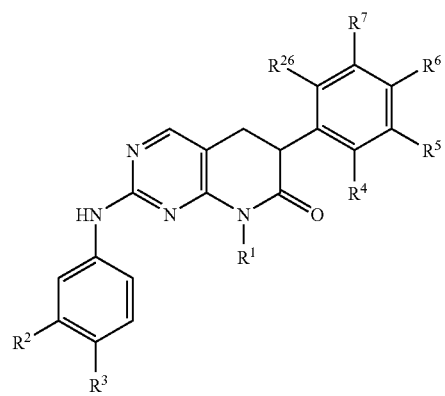

with the proviso that Ar is not 2-pyridyl or substituted 2-pyridyl.

The present invention also relates to pharmaceutical compositions comprising a therapeutically effective amount of one or more compounds of formulas I and II, and a pharmaceutically acceptable carrier or excipient.

The present invention further relates to a method for treating solid tumors, in particular breast, lung, prostate or colon tumors, by administering to a human patient in need of such therapy an effective amount of a compound of formulas I or II, and/or a pharmaceutically acceptable salt thereof.

The present invention is further directed to novel intermediate compounds useful in the preparation of compounds of formulas I and II.

DETAILED DESCRIPTION OF THE INVENTION

Definitions

As used herein, the following terms shall have the following definitions. "Alkenyl" denotes a straight-chain or branched aliphatic hydrocarbon having at least one set of carbon-carbon double bond, for example vinyl, 2-butenyl, and 3-methyl-2-butenyl.

"Alkynyl" denotes a straight-chain or branched aliphatic hydrocarbon having at least one set of carbon-carbon triple bond, for example ethynyl, and 2-butenyl.

"Alkyl" denotes a straight-chain or branched saturated aliphatic hydrocarbon having 1 to 10, preferably 1 to 6, and more preferably 1 to 4 carbon atoms. Alkyl groups having 1 to 6 carbon atoms are also referred to herein as "lower alkyl." Typical lower alkyl groups include methyl, ethyl, propyl, isopropyl, butyl, t-butyl, 2-butyl, pentyl and hexyl. As used herein the sample designation $C_{1-4}$ alkyl means alkyl having from 1 to 4 carbon atoms.

"Alkoxy" means an alkyl radical that is attached to the remainder of the molecule by oxygen (RO—), e.g. methoxy, ethoxy.

"Aryl" means an aromatic carbocyclic radical, for example a 6–10 membered aromatic or partially aromatic ring system. A partially aromatic ring system is one with two fused rings with one of the two rings being aromatic, for example tetrahydronaphthyl. Preferred aryl groups include, but are not limited to, phenyl, naphthyl, tolyl and xylyl.

"Cycloalkyl" means a non-aromatic, partially or completely saturated cyclic aliphatic hydrocarbon group containing 3 to 8 atoms. Examples of cycloalkyl groups include cyclopropyl, cyclopentyl and cyclohexyl.

"Effective amount" or "Therapeutically Effective amount" means an amount of at least one compound for formulas I and II, or a pharmaceutically acceptable salt or ester thereof, that significantly inhibits proliferation of tumor cells, including human tumor cell lines.

"Halogen" means fluorine, chlorine, bromine or iodine, preferably chlorine or fluorine.

"Hetero atom" means an atom selected from N, O and S, preferably N. If the hetero atom is N, it can be present as —NH— or —N-lower alkyl-. If the hetero atom is S, it can be present as S, SO or $SO_2$.

"Heteroaryl" means an aromatic heterocyclic ring system containing up to two rings. Preferred heteroaryl groups include, but are not limited to, thienyl, furyl, indolyl, pyrrolyl, pyridinyl, pyrazinyl, oxazolyl, thiaxolyl, quinolinyl, pyrimidinyl, imidazole and tetrazolyl.

"Heterocycle" or "heterocyclyl" means a 3- to 10-membered saturated or partially unsaturated non-aromatic monovalent cyclic radical having from one to 3 hetero atoms selected from nitrogen, oxygen or sulfur or a combination thereof Examples of preferred heterocycles are piperidine, piperazine, pyrrolidine, and morpholine.

"Hydroxy" is a prefix indicating the presence of a monovalent OH group.

"$IC_{50}$" refers to the concentration of a particular compound according to the invention required to inhibit 50% of a specific measured activity. $IC_{50}$ can be measured, inter alia, as is described in Example 15, infra.

"Pharmaceutically acceptable salt" refers to conventional acid-addition salts or base-addition salts that retain the biological effectiveness and properties of the compounds of formula I and are formed from suitable non-toxic organic or inorganic acids or organic or inorganic bases. Sample acid-addition salts include those derived from inorganic acids such as hydrochloric acid, hydrobromic acid, hydroiodic acid, sulfuric acid, sulfamic acid, phosphoric acid and nitric acid, and those derived from organic acids such as p-toluenesulfonic acid, salicylic acid, methanesulfonic acid, oxalic acid, succinic acid, citric acid, malic acid, lactic acid, fumaric acid, and the like. Sample base-addition salts include those derived from ammonium, potassium, sodium and, quaternary ammonium hydroxides, such as for example, tetramethylammonium hydroxide. The chemical modification of a pharmaceutical compound (i.e. drug) into a salt is a technique well known to pharmaceutical chemists to obtain improved physical and chemical stability, hygroscopicity, flowability and solubility of compounds. See, e.g., H. Ansel et. al., Pharmaceutical Dosage Forms and Drug Delivery Systems (6th Ed. 1995) at pp. 196 and 1456–1457.

"Pharmaceutically acceptable," such as pharmaceutically acceptable carrier, excipient, etc., means pharmacologically acceptable and substantially non-toxic to the subject to which the particular compound is administered.

"Substituted," as in, for example, substituted alkyl, lower alkyl, aryl, cycloalkyl, cycloaryl and heteroaryl, means that the substitution can occur at one or more positions and, unless otherwise indicated, that the substituents at each substitution site are independently selected from the specified options.

In one embodiment, this invention relates to compound of formula

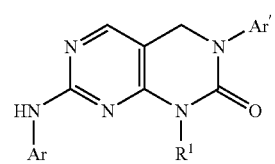

I or a pharmaceutically acceptable salt thereof, wherein

Ar and Ar' are independently selected from the group consisting of aryl, substituted aryl, heteroaryl and substituted heteroaryl;

with the proviso that for Ar, the heteroaryl is not 2-pyridyl and substituted heteroaryl is not substituted 2-pyridyl.

$R^1$ is selected from the group consisting of

H;

$C_{1-10}$ alkyl;

$C_{1-10}$ alkyl independently substituted by up to three groups selected from aryl, heteroaryl, heterocycle, cycloalkyl, $NR^8R^9$, $OR^{10}$, $SR^{10}$, halogen, $COR^{11}$, $CO_2R^{11}$, $CONR^{11}R^{12}$, $SO_2NR^{11}R^{12}$, $SOR^{11}$, $SO_2R^{11}$, CN and $NO_2$, wherein the aryl, heteroaryl, heterocycle and cycloalkyl groups may each independently be substituted by up to three groups selected from $NR^8R^9$, $OR^{10}$, $SR^{10}$, halogen, $COR^{11}$, $CO_2R^{11}$, $CONR^{11}R^{12}$, $SO_2NR^{11}R^{12}$, $SOR^{11}$, $SO_2R^{11}$, CN and $NO_2$;

aryl;

aryl independently substituted by up to three groups selected from lower alkyl, $NR^8R^9$, $OR^{10}$, $SR^{10}$, halogen, $COR^{11}$, $CO_2R^{11}$, $CONR^{11}R^{12}$, $SO_2NR^{11}R^{12}$, $SOR^{11}$, $SO_2R^{11}$, CN and $NO_2$;

heteroaryl;

heteroaryl independently substituted by up to three groups selected from lower alkyl, $NR^8R^9$, $OR^{10}$, $SR^{10}$, halogen, $COR^{11}$, $CO_2R^{11}$, $CONR^{11}R^{12}$, $SO_2NR^{11}R^{12}$, $SOR^{11}$, $SO_2R^{11}$, CN and $NO_2$;

heterocycle;

heterocycle independently substituted by up to three groups selected from lower alkyl, $NR^8R^9$, $OR^{10}$, $SR^{10}$, halogen, $COR^{11}$, $CO_2R^{11}$, $CONR^{11}R^{12}$, $SO_2NR^{11}R^{12}$, $SOR^{11}$, $SO_2R^{11}$, CN and $NO_2$;

$C_{3-10}$ cycloalkyl;

$C_{3-10}$ cycloalkyl independently substituted by up to three groups selected from lower alkyl, substituted lower alkyl, $NR^8R^9$, $OR^{10}$, $SR^{10}$, halogen, $COR^{11}$, $CO_2R^{11}$, $CONR^{11}R^{12}$, $SO_2NR^{11}R^{12}$, $SOR^{11}$, $SO_2R^{11}$, CN and $NO_2$;

$C_{2-10}$ alkenyl;

$C_{2-10}$ alkenyl independently substituted by up to three groups selected from cycloalkyl, substituted cycloalkyl, heterocyclyl, substituted heterocycloalkyl, $NR^8R^9$, $OR^{10}$, $SR^{10}$, halogen, $COR^{11}$, $CO_2R^{11}$, $CONR^{11}R^{12}$, $SO_2NR^{11}R^{12}$, $SOR^{11}$, $SO_2R^{11}$, CN and $NO_2$;

$C_{2-10}$ alkynyl; and $C_{2-10}$ alkynyl independently substituted by up to three groups selected from $NR^8R^9$, $OR^{10}$, $SR^{10}$, halogen, $COR^{11}$, $CO_2R^{11}$, $CONR^{11}R^{12}$, $SO_2NR^{11}R^{12}$, $SOR^{11}$, $SO_2R^{11}$, CN and $NO_2$; and wherein $R^8$, $R^9$ and $R^{10}$ are independently H or lower alkyl;

$R^{11}$ and $R^{12}$ are independently selected from the group consisting of

H;

unsubstituted lower alkyl;

lower alkyl substituted by hydroxy, alkoxy or $NR^{21}R^{22}$;

unsubstituted cycloalkyl;

cycloalkyl substituted by hydroxy, alkoxy, lower alkyl or $NR^{21}R^{22}$;

unsubstituted heterocycle;

heterocycle substituted by hydroxy, alkoxy, lower alkyl or $NR^{21}R^{22}$;

or alternatively $NR^{11}R^{12}$ forms a ring having 3 to 7 atoms, the ring having no or at least one additional heteroatoms, with the proviso that if the heteroatom is N, the heteroatom may be substituted by one or more substituents selected from the group consisting of lower alkyl, $OR^{13}$, $COR^{14}$, $CO_2R^{14}$, $CONR^{14}R^{15}$, $SO_2R^{14}$, and $SO_2NR^{14}R^{15}$;

$R^{13}$ is selected from the group consisting of

H;

$COR^{14}$;

$CONR^{14}R^{15}$;

unsubstituted lower alkyl;

lower alkyl substituted by hydroxy, alkoxy or $NR^{21}R^{22}$;

unsubstituted cycloalkyl;

cycloalkyl substituted by hydroxy, alkoxy, lower alkyl or $NR^{21}R^{22}$, unsubstituted heterocycle; and heterocycle substituted by hydroxy, alkoxy, lower alkyl or $NR^{21}R^{22}$;

$R^{14}$ and $R^{15}$ are independently selected from the group consisting of

H;

unsubstituted lower alkyl;

lower alkyl substituted by hydroxy, alkoxy or $NR^{21}R^{22}$;

unsubstituted cycloalkyl;

cycloalkyl substituted by hydroxy, alkoxy, lower alkyl or $NR^{21}R^{22}$;

unsubstituted heterocycle;

heterocycle substituted by hydroxy, alkoxy, lower alkyl or $NR^{21}R^{22}$;

or alternatively $NR^{14}R^{15}$ forms a ring having 3 to 7 atoms, the ring having no or at least one hetero atoms, with the proviso that if the heteroatom is N, the heteroatom may be substituted by one or more substituents selected from the group consisting of lower alkyl, $OR^{23}$, $COR^{23}$, $CO_2R^{23}$, $CONR^{23}R^{24}$, $SO_2R^{23}$, $SO_2NR^{23}R^{24}$;

$R^{21}$ is selected from the group consisting of H, lower alkyl, $COR^{23}$ or $CO_2R^{23}$;

$R^{22}$, $R^{23}$ and $R^{24}$ are independently selected from the group consisting of H or lower alkyl, or alternatively $NR^{21}R^{22}$ or $NR^{23}R^{24}$ independently forms a ring having 3 to 7 atoms, the ring having no or at least one additional hetero atoms selected from the group consisting of N, O, or S, with the proviso that if the heteroatom is N, the heteroatom may be in the form of —NH or $NR^{25}$, and if the hetero atom is S, it may be in the form of $S(O)_m$ where m=0, 1 or 2; and $R^{25}$ is lower alkyl.

In another embodiment, this invention relates to compounds of formula

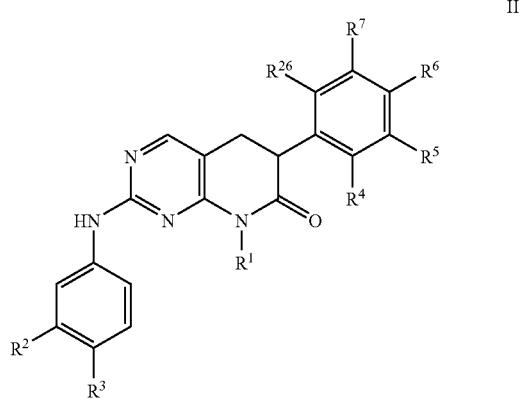

II or a pharmaceutically acceptable salt thereof, where $R^1$ is selected from the group consisting of

H;

$C_{1-10}$ alkyl;

$C_{1-10}$ alkyl independently substituted by up to three groups selected from aryl, heteroaryl, heterocycle, cycloalkyl, $NR^8R^9$, $OR^{10}$, $SR^{10}$, halogen, $COR^{11}$, $CO_2R^{11}$, $CONR^{11}R^{12}$, $SO_2NR^{11}R^{12}$, $SOR^{11}$, $SO_2R^{11}$, CN and $NO_2$, wherein the aryl, heteroaryl, heterocycle and cycloalkyl groups may each independently be substituted by up to three groups selected from $NR^8R^9$, $OR^{10}$, $SR^{10}$, halogen, $COR^{11}$, $CO_2R^{11}$, $CONR^{11}R^{12}$, $SO_2NR^{11}R^{12}$, $SOR^{11}$, $SO_2R^{11}$, CN and $NO_2$;

aryl;

aryl independently substituted by up to three groups selected from lower alkyl, $NR^8R^9$, $OR^{10}$, $SR^{10}$, halogen, $COR^{11}$, $CO_2R^{11}$, $CONR^{11}R^{12}$, $SO_2NR^{11}R^{12}$, $SOR^{11}$, $SO_2R^{11}$, CN and $NO_2$;

heteroaryl;

heteroaryl independently substituted by up to three groups selected from lower alkyl, $NR^8R^9$, $OR^{10}$, $SR^{10}$, halogen, $COR^{11}$, $CO_2R^{11}$, $CONR^{11}R^{12}$, $SO_2NR^{11}R^{12}$, $SOR^{11}$, $SO_2R^{11}$, CN and $NO_2$;

heterocycle;

heterocycle independently substituted by up to three groups selected from lower alkyl, $NR^8R^9$, $OR^{10}$, $SR^{10}$, halogen, $COR^{11}$, $CO_2R^{11}$, $CONR^{11}R^{12}$, $SO_2NR^{11}R^{12}$, $SOR^{11}$, $SO_2R^{11}$, CN and $NO_2$;

$C_{3-10}$ cycloalkyl;

$C_{3-10}$ cycloalkyl independently substituted by up to three groups selected from lower alkyl, substituted lower alkyl, $NR^8R^9$, $OR^{10}$, $SR^{10}$, halogen, $COR^{11}$, $CO_2R^{11}$, $CONR^{11}R^{12}$, $SO_2NR^{11}R^{12}$, $SOR^{11}$, $SO_2R^{11}$, CN and $NO_2$;

$C_{2-10}$ alkenyl;

$C_{2-10}$ alkenyl independently substituted by up to three groups selected from cycloalkyl, substituted cycloalkyl, heterocyclyl, substituted heterocycloalkyl, $NR^8R^9$, $OR^{10}$, $SR^{10}$, halogen, $COR^{11}$, $CO_2R^{11}$, $CONR^{11}R^{12}$, $SO_2NR^{11}R^{12}$, $SOR^{11}$, $SO_2R^{11}$, CN and $NO_2$;

$C_{2-10}$ alkynyl; and $C_{2-10}$ alkynyl independently substituted by up to three groups selected from $NR^8R^9$, $OR^{10}$, $SR^{10}$, halogen, $COR^{11}$, $CO_2R^{11}$, $CONR^{11}R^{12}$, $SO_2NR^{11}R^{12}$, $SOR^{11}$, $SO_2R^{11}$, CN and $NO_2$; and wherein $R^8$, $R^9$ and $R^{10}$ are independently H or lower alkyl;

$R^2$ and $R^3$ are independently selected from the group consisting of
$NR^{11}R^{12}$;
$OR^{13}$;
$SR^{16}$;
halogen;
$COR^{14}$;
$CO_2R^{14}$;
$CONR^{14}R^{15}$;
$SO_2NR^{14}R^{15}$;
$SO_2R^{14}$;
CN;
$NO_2$;
$(CH_2)_n$heteroaryl;
$(CH_2)_n$heterocycle;
$C_1$–$C_{10}$ alkyl;
$C_3$–$C_{10}$ cycloalkyl;
$C_2$–$C_{10}$ alkenyl;
$C_2$–$C_{10}$ alkynyl;
where n is 0, 1, 2, or 3 and the aryl, heteroaryl, heterocycle, alkyl, cycloalkyl, alkenyl, and alkynyl groups are unsubstituted or substituted by up to three groups selected from
$NR^{11}R^{12}$;
$OR^{13}$;
$SR^{16}$;
halogen;
$COR^{14}$;
$CO_2R^{14}$;
$CONR^{14}R^{15}$;
$SO_2NR^{14}R^{15}$;
$SO_2R^{14}$;
CN; and
$NO_2$;
or alternatively, $R^2$ and $R^3$ together form a ring having 3 to 7 atoms fused to the phenyl ring that they are attached to, the ring having no or at least one additional hetero atoms, with the proviso that if the heteroatom is N, the heteroatom may be substituted by at least one substituent selected from the group consisting of lower alkyl;
lower alkyl substituted by hydroxy, alkoxy or $NR^{11}R^{12}$;
$NR^{11}R^{12}$;
$OR^{13}$;
$SR^{16}$;
$COR^{14}$;
$CO_2R^{14}$;
$CONR^{14}R^{15}$;
$SO_2NR^{14}R^{15}$;
$SO_2R^{14}$; and
CN;
$R^4$, $R^5$, $R^6$, $R^7$ and $R^{26}$ are independently selected from the group, with at least one being H, consisting of
H;
unsubstituted lower alkyl;
lower alkyl substituted by hydroxy, alkoxy or halogen;
$NR^{21}R^{22}$;
$OR^{23}$;
$SR^{23}$;
halogen;
$NO_2$;
$COR^{23}$;
$CO_2R^{23}$;
$CONR^{23}R^{24}$;
$SO_2NR^{23}R^{24}$;
$SO_2R^{23}$; and
CN;

$R^{11}$ and $R^{12}$ are independently selected from the group consisting of
H;
unsubstituted lower alkyl;
lower alkyl substituted by hydroxy, alkoxy or $NR^{21}R^{22}$;
unsubstituted cycloalkyl;
cycloalkyl substituted by hydroxy, alkoxy, lower alkyl or $NR^{21}R^{22}$;
unsubstituted heterocycle; and
heterocycle substituted by hydroxy, alkoxy, lower alkyl or $NR^{21}R^{22}$;
or alternatively $NR^{11}R^{12}$ forms a ring having 3 to 7 atoms, the ring having no or at least one additional hetero atoms, with the proviso that if the heteroatom is N, the heteroatom may be substituted by one or more substituents selected from the group consisting of lower alkyl, $COR^{14}$, $CO_2R^{14}$, $CONR^{14}R^{15}$, $SO_2R^{14}$, $SO_2NR^{14}R^{15}$;
$R^{13}$ is selected from the group consisting of
H;
$COR^{14}$;
$CONR^{14}R^{15}$;
unsubstituted lower alkyl;
lower alkyl substituted by hydroxy, alkoxy or $NR^{21}R^{22}$,
unsubstituted cycloalkyl;
cycloalkyl substituted by hydroxy, alkoxy, lower alkyl or $NR^{21}R^{22}$,
unsubstituted heterocycle; and
heterocycle substituted by hydroxy, alkoxy, lower alkyl or $NR^{21}R^{22}$;
$R^{14}$ and $R^{15}$ are independently selected from the group consisting of
H;
unsubstituted lower alkyl;
lower alkyl substituted by hydroxy, alkoxy or $NR^{21}R^{22}$;
unsubstituted cycloalkyl;
cycloalkyl substituted by hydroxy, alkoxy, lower alkyl or $NR^{21}R^{22}$;
unsubstituted heterocycle; and
heterocycle substituted by hydroxy, alkoxy, lower alkyl or $NR^{21}R^{22}$, or alternatively $NR^{14}R^{15}$ forms a ring having 3 to 7 atoms, the ring having no or at least one additional heteroatoms, with the proviso that if the heteroatom is N, the heteroatom may be substituted by one or more substituents selected from the group consisting of lower alkyl, $COR^{23}$, $CO_2R^{23}$, $CONR^{23}R^{24}$, $SO_2R^{23}$, $SO_2NR^{23}R^{24}$;
$R^{16}$ is selected from the group consisting of
unsubstituted lower alkyl;
lower alkyl substituted by hydroxy, alkoxy or $NR^{21}R^{22}$,
unsubstituted cycloalkyl;
cycloalkyl substituted by hydroxy, alkoxy, lower alkyl or $NR^{21}R^{22}$,
unsubstituted heterocycle; and
heterocycle substituted by hydroxy, alkoxy, lower alkyl or $NR^{21}R^{22}$;
$R^{21}$ is selected from the group consisting of H, lower alkyl, $COR^{23}$ or $CO_2R^{23}$;
$R^{22}$, $R^{23}$ and $R^{24}$ are independently selected from the group consisting of H or lower alkyl, or alternatively $NR^{21}R^{22}$ or $NR^{23}R^{24}$ independently forms a ring having 3 to 7 atoms, the ring having no or at least one additional heteroatom selected from the group consisting of N, O, and S, with the proviso that if the heteroatom is N, the heteroatom may be in the form of —NH or $NR^{25}$, and if the hetero atom is S, it may be in the form of $S(O)_m$ where m=0, 1 or 2; and
$R^{25}$ is lower alkyl.

In one embodiment, this invention is directed to a pharmaceutical composition comprising a therapeutically effective amount of the compounds above and a pharmaceutically acceptable carrier or excipient.

In another embodiment, this invention is directed to a method for treating cancer comprising administering to a patient in need of such treatment a therapeutically effective amount of the compounds above. The cancer is breast, lung, colon or prostate.

In yet another embodiment, this invention is directed to a method of controlling cancer comprising administering to a patient in need of such treatment a therapeutically effective amount of the compounds above. The cancer is breast, lung, colon or prostate.

The following compounds are preferred embodiments according to the present invention:
6-(4-Methoxy-phenyl)-8-phenyl-2-phenylamino-5,8-dihydro-6H-pyrido[2,3-d]pyrimidin-7-one (Example 1f);
6-(2,6-Dichloro-phenyl)-8-phenyl-2-phenylamino-5,8-dihydro-6H-pyrido[2,3-d]pyrimidin-7-one (Example 2c);
6-(3,5-Dimethoxy-phenyl)-8-phenyl-2-phenylamino-5,8-dihydro-6H-pyrido[2,3-d]pyrimidin-7-one (Example 3d);
8-Phenyl-2-phenylamino-6-O-tolyl-5,8-dihydro-6H-pyrido[2,3-d]pyrimidin-7-one (Example 4c);
6,8-Diphenyl-2-phenylamino-5,8-dihydro-6H-pyrido[2,3-d]pyrimidin-7-one (Example 5c);
6-(2,5-Dimethoxy-phenyl)-8-phenyl-2-phenylamino-5,8-dihydro-6H-pyrido[2,3-d]pyrimidin-7-one (Example 6c);
6-(2-Methoxy-phenyl)-8-phenyl-2-phenylamino-5,8-dihydro-6H-pyrido[2,3-d]pyrimidin-7-one (Example 7c);
6-(3,5-Bis-trifluromethyl-phenyl)-8-phenyl-2-phenylamino-5,8-dihydro-6H-pyrido[2,3-d]pyrimidin-7-one (example 8d);
8-Phenyl-2-phenylamino-6-pyridin-4-yl-5,8-dihydro-6H-pyrido[2,3-d]pyrimidin-7-one (Example 9c);
8-Phenyl-2-phenylamino-6-pyridin-3-yl-5,8-dihydro-6H-pyrido[2,3-d]pyrimidin-7-one (Example 10c);
6-(3,4-Dimethoxy-phenyl)-8-phenyl-2-phenylamino-5,8-dihydro-6H-pyrido[2,3-d]pyrimidin-7-one (Example 11c);
6-(4-Methoxy-phenyl)-2-(6-methoxy-pyridin-3-ylamino)-8-phenyl-5,8-dihydro-6H-pyrido[2,3-d]pyrimidine-7-one (Example 12d);
8-Isobutyl-6-(4-methoxy-phenyl)-2-phenylamino-5,8-dihydro-6H-pyrido[2,3-d]pyrimidine-7-one (Example 13b); and
8–Cyclopropylmethyl-6-(4-methoxy-phenyl)-2-phenylamino-5,8-dihydro-6H-pyrido[2,3-d]pyrimidine-7-one (Example 14b).

General Synthesis of Compounds According to the Invention

The compounds of the present invention can be prepared by any conventional means. Suitable processes for synthesizing these compounds are provided in the examples. Generally, compounds of Formula I can be prepared according to the below-described synthetic route.

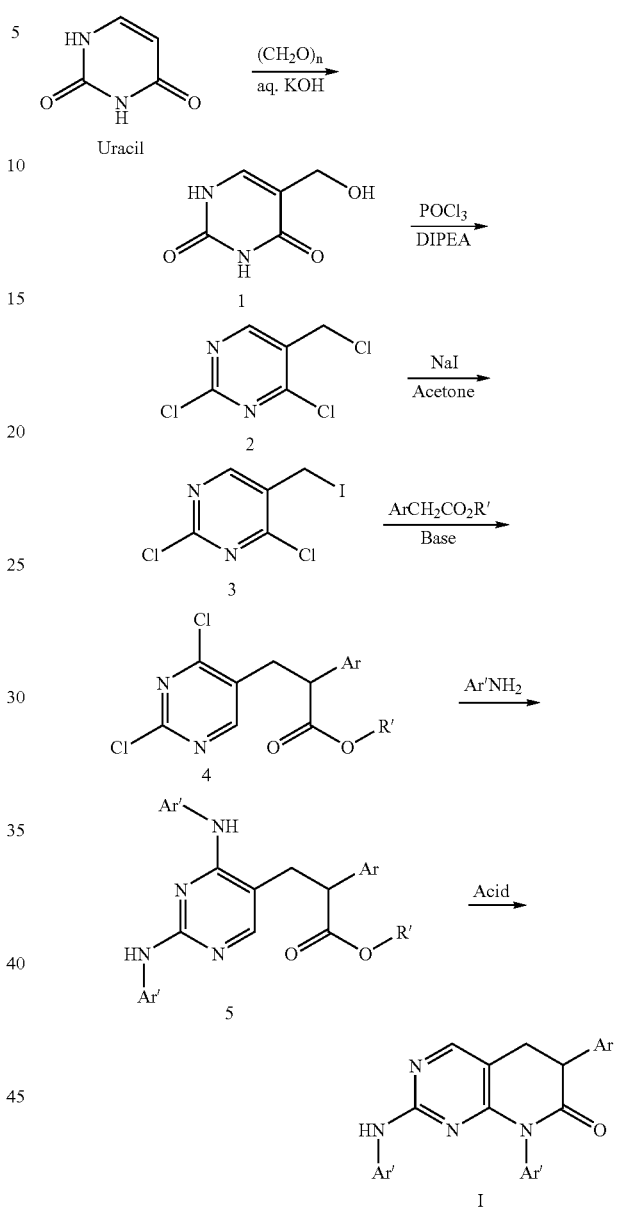

Scheme 1

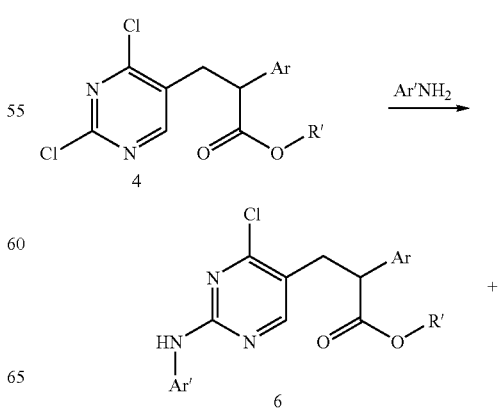

Scheme 2

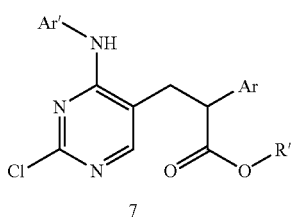

Scheme 3

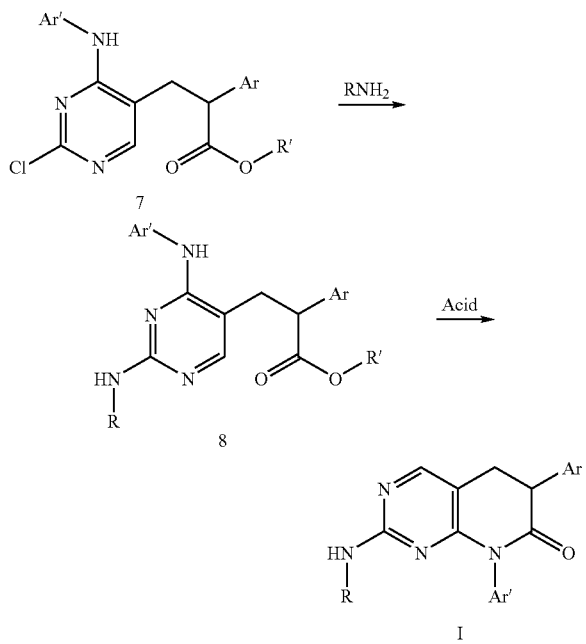

Scheme 4

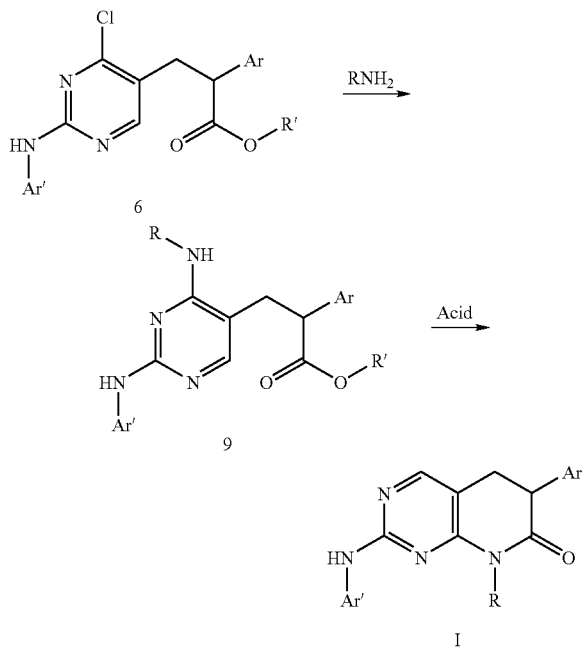

Compositions/Formulations

In an alternative embodiment, the present invention relates to pharmaceutical compositions comprising at least one compound of formula I, or a pharmaceutically acceptable salt or ester thereof.

These pharmaceutical compositions can be administered orally, for example in the form of tablets, coated tablets, dragees, hard or soft gelatin capsules, solutions, emulsions or suspensions. They can also be administered rectally, for example, in the form of suppositories, or parenterally, for example, in the form of injection solutions.

The pharmaceutical compositions of the present invention comprising compounds of formulas I and II, and/or the salts thereof, may be manufactured in a manner that is known in the art, e.g., by means of conventional mixing, encapsulating, dissolving, granulating, emulsifying, entrapping, dragee-making, or lyophilizing processes. These pharmaceutical preparations can be formulated with therapeutically inert, inorganic or organic carriers. Lactose, corn starch or derivatives thereof, talc, stearic acid or its salts can be used as such carriers for tablets, coated tablets, dragees and hard gelatin capsules. Suitable carriers for soft gelatin capsules include vegetable oils, waxes and fats. Depending on the nature of the active substance, no carriers are generally required in the case of soft gelatin capsules. Suitable carriers for the manufacture of solutions and syrups are water, polyols, saccharose, invert sugar and glucose. Suitable carriers for injection are water, alcohols, polyols, glycerine, vegetable oils, phospholipids and surfactants. Suitable carriers for suppositories are natural or hardened oils, waxes, fats and semi-liquid polyols.

The pharmaceutical preparations can also contain preserving agents, solubilizing agents, stabilizing agents, wetting agents, emulsifying agents, sweetening agents, coloring agents, flavoring agents, salts for varying the osmotic pressure, buffers, coating agents or antioxidants. They can also contain other therapeutically valuable substances, including additional active ingredients other than those of formulas I and II.

Dosages

As mentioned above, the compounds of the present invention, including the compounds of formula I, are useful in the treatment or control of cell proliferative disorders, in particular oncological disorders. These compounds and formulations containing said compounds are particularly useful in the treatment or control of solid tumors, such as, for example, breast, colon, lung and prostate tumors. Thus, the present invention is further directed to a method for treating such solid tumors by administering to a patient in need of such therapy an effective amount of a compound of formulas I and II, and/or their salt.

A therapeutically effective amount of a compound in accordance with this invention means an amount of compound that is effective to prevent, alleviate or ameliorate symptoms of disease or prolong the survival of the subject being treated. Determination of a therapeutically effective amount is within the skill in the art.

The therapeutically effective amount or dosage of a compound according to this invention can vary within wide limits and may be determined in a manner known in the art. Such dosage will be adjusted to the individual requirements in each particular case including the specific compound(s) being administered, the route of administration, the condition being treated, as well as the patient being treated. In general, in the case of oral or parenteral administration to adult humans weighing approximately 70 Kg, a daily dosage of about 10 mg to about 10,000 mg, preferably from about 200 mg to about 1,000 mg, should be appropriate, although the upper limit may be exceeded when indicated. The daily dosage can be administered as a single dose or in divided doses, or for parenteral administration, it may be given as continuous infusion.

The present invention is also directed to the following novel intermediates useful in the synthesis of compounds of formulas I and II:

3-(2,4-Dichloro-pyrimidin-5-yl)-2-(4-methoxy-phenyl)-propionic acid methyl ester (Example 1d);
3-(2,4-Diphenylamino-pyrimidin-5-yl)-2-(4-methoxy-phenyl)-propionic acid methyl ester (Example 1e);
2-(2,6-Dichloro-phenyl)-3-(2,4-dichloro-pyrimidin-5-yl)-propionic acid methyl ester (Example 2a);
3-(2,4-Diphenylamino-pyrimidin-5-yl)-2-(2,6-Dichloro-phenyl)-propionic acid methyl ester (Example 2b);
3-(2,4-Dichloro-pyrimidin-5-yl)-2-(3,5-dimethoxy-phenyl)-propionic acid methyl ester (Example 3b);
3-(2,4-Diphenylamino-pyrimidin-5-yl)-2-(3,5-dimethoxy-phenyl)-propionic acid methyl ester (Example 3c);
3-(2,4-Dichloro-pyrimidin-5-yl)-2-O-tolyl-propionic acid methyl ester (Example 4a);
3-(2,4-Diphenylamino-pyrimidin-5-yl)-2-O-tolyl-propionic acid methyl ester (Example 4b)
3-(2,4-Dichloro-pyrimidin-5-yl)-2-phenyl-propionic acid methyl ester (Example 5a);
3-(2,4-Diphenylamino-pyrimidin-5-yl)-2-phenyl-propionic acid methyl ester (Example 5b);
3-(2,4-Dichloro-pyrimidin-5-yl)-2-(2,5-dimethoxy-phenyl)-propionic acid ethyl ester (Example 6a);
3-(2,4-Diphenylamino-pyrimidin-5-yl)-2-(2,5-dimethoxy-phenyl propionic acid ethyl ester (Example 6b);
3-(2,4-Dichloro-pyrimidin-5-yl)-2-(2-methoxy-phenyl)-propionic acid ethyl ester (Example 7a);
3-(2,4-Diphenylamino-pyrimidin-5-yl)-2-(2-methoxy-phenyl) propionic acid ethyl ester (Example 7b);
2-(3,5-Bis-trifluoromethyl-phenyl)-3-(2,4-dichloro-pyrimidin-5-yl)-propionic acid methyl ester (Example 8b);
3-(2,4-Diphenylamino-pyrimidin-5-yl)-2-(3,5-bis-trifluoromethyl-phenyl)-propionic acid methyl ester (Example 8c);
3-(2,4-Dichloro-pyrimidin-5-yl)-2-pyridin-4-yl-propionic acid ethyl ester (Example 9a);
3-(2,4-Diphenylamino-pyrimidin-5-yl)-2-pyridin-4-yl-propionic acid ethyl ester (Example 9b);
3-(2,4-Dichloro-pyrimidin-5-yl)-2-pyridin-3-yl-propionic acid ethyl ester (Example 10a);
3-(2,4-Diphenylamino-pyrimidin-5-yl)-2-pyridin-3-yl-propionic acid ethyl ester (Example 10b)
3-(2,4-Dichloro-pyrimidin-5-yl)-2-(3,4-dimethoxy-phenyl)-propionic acid ethyl ester (Example 11a);
3-(2,4-Diphenylamino-pyrimidin-5-yl)-2-(3,4-dimethoxy-phenyl)-propionic acid ethyl ester (Example 11b);
3-(4–Chloro-2-phenylamino-pyrimidin-5-yl)-2-(4-methoxy-phenyl)-propionic acid methyl ester (Example 12a);
3-(2–Chloro-4-phenylamino-pyrimidin-5-yl)-2-(4-methoxy-phenyl)-propionic acid methyl ester (Example 12b);
3-[2-(6-Methoxy-pyridin-3-ylamino)-4-phenylamino-pyrimidin-5-yl]-2-(4-methoxy-phenyl)-propionic acid methyl ester (Example 12c);
3-(2-Phenylamino-4-isobutylamino-pyrimidin-5-yl)-2-(4-methoxy-phenyl)-propionic acid methyl ester (Example 13a); and
3-(2-Phenylamino-4-cyclopropylmethylamino-pyrimidin-5-yl)-2-(4-methoxy-phenyl)-propionic acid methyl ester (Example 14a).

EXAMPLES

The following examples illustrate preferred methods for synthesizing the compounds and formulations of the present invention.

Example 1a 5-(Hydroxymethyl)-1,3-dihydropyrimidine-2,4-dione

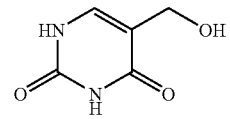

A 2-L, three-necked flask equipped with a mechanical stirrer, thermometer, condenser, and nitrogen-inlet bubbler was charged with uracil (185.0 g, 1650 mmol) (Aldrich), paraformaldehyde (61.50 g, 2050 mmol as formaldehyde) (Aldrich), and a solution of potassium hydroxide (86.9%, 59.95 g, 928.5 mmol) (Aldrich) in water (1.445 L). The mixture was stirred at 50–52° C. for 68 hours. TLC analysis indicated complete reaction. After concentration at 60° C./14 mm Hg to a volume of ca. 500 mL, the residue was diluted with acetone (500 mL). The resulting precipitate was collected by filtration, washed with acetone, and dried by suction, then at 50° C./25 mm Hg to give crude 5-(hydroxymethyl)-1,3-dihydropyrimidine-2,4-dione (250 g) as a white solid. The combined mother liquor and washes were concentrated to a volume of ca. 100 mL and a solution of hydroxylamine hydrochloride (27.52 g, 396.0 mmol, Aldrich) in water (100 mL) was added. The resulting precipitate was collected by filtration, washed with acetone, and dried by suction to give second crop of crude 5-(hydroxymethyl)-1,3-dihydropyrimidine-2,4-dione (34 g) as a white solid. The two lots were combined (244 g, 4% overweight) and used directly in the next step.

Example 1b 2,4-Dichloro-5-(chloromethyl)pyrimidine

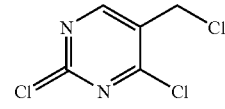

Caution: This compound is highly caustic.

A 1-L, three-necked flask equipped with a mechanical stirrer, addition funnel, thermometer and nitrogen-inlet bubbler was charged with crude 5-(hydroxymethyl)-1,3-dihydropyrimidine-2,4-dione (50.25 g, ca. 340 mmol) (from Example 1a supra), phosphorous oxychloride (164.8 mL, 1768 mmol) (Aldrich), and toluene (100 mL). To this mixture was added N,N-diisopropylethylamine (184.7 mL, 1060 mmol) (Aldrich) over 10 min, while maintaining the temperature of the mixture below 70° C. using a water bath. After completion of the addition, the cooling bath was removed and the mixture was heated to reflux (113–116° C.) for 1 hour. Some of the toluene (ca. 35 mL) was removed by distillation to increase the temperature of the reaction mixture to 120° C. and the mixture was stirred at 120–123° C. for 5 hours. TLC analysis indicated reaction was complete. After the mixture was allowed to cool to room temperature overnight, the mixture was cautiously added, over 67 minutes, to a stirred bi-phasic mixture of water (200 mL) and isopropyl acetate (150 mL), while maintaining the temperature between 17° C. to 21° C. using an ice-water bath. After stirring at 18–21° C. for 80 minutes with occasional ice-water cooling, the mixture was extracted with toluene (4×150 mL). The combined organic layers were dried (sodium sulfate), filtered, then concentrated to dryness under reduced pressure to give of crude 2,4-dichloro-5-(chloromethyl)pyrimidine as a white solid, containing polar impurities. (Yield 56.1 g, 83.6% yield from uracil).

Crude 2,4-dichloro-5-(chloromethyl)pyrimidine (70.39 g) was dissolved in dichloromethane (80 mL) and the resulting solution was filtered through a pad of TLC grade silica gel (100 g). The silica gel was then washed with dichloromethane: hexanes (1 L, 7:3), and the combined filtrate and washes were concentrated to dryness under reduced pressure to give 2,4-dichloro-5-(chloromethyl)pyrimidine as a white solid. (Yield 58.77 g, 83.5% recovery, 69.8% overall yield from uracil).

Example 1c 2,4-Dichloro-5-(iodomethyl)pyrimidine

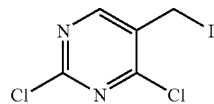

A 500-mL, round-bottom flask equipped with a magnetic stirrer, condenser, and nitrogen-inlet bubbler was charged with sodium iodide (38.5 g, 256.9 mmol) (Aldrich) and acetone (300 mL). After a clear solution was obtained, 2,4-dichloro-5-(chloromethyl)pyrimidine (50.0 g, 253.2 mmol) (from Example 1b supra) was added in one portion. After stirring at room temperature for 20 minutes, the mixture was heated to reflux for 15 minutes. NMR analysis indicated 98% conversion. After cooling to room temperature, the resulting precipitate (sodium chloride) was removed by filtration through a medium-sintered glass funnel and washed with acetone. The combined filtrate and washes were concentrated to a weight of ca. 75 g. The resulting concentrated solution of 2,4-dichloro-5-(iodomethyl)pyrimidine in acetone was diluted with toluene (20 mL). After concentration to a weight of ca.85 g in order to remove the residual acetone, this concentrated solution of 2,4-dichloro-5-(iodomethyl)pyrimidine in toluene was used directly in the next step.

Example 1d 3-(2,4-Dichloro-pyrimidin-5-yl)-2-(4-methoxy-phenyl)-propionic acid methyl ester

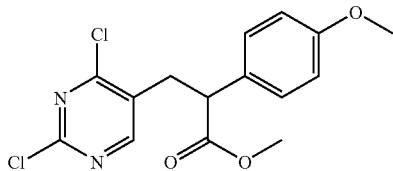

To a solution of N-isopropylcyclohexylamine (720 mg, 5.0 mmol) (Aldrich) in dry tetrahydrofuran (10 mL) was added n-butyllithium (2.5 M in hexanes, 2.0 mL, 5.0 mmol) (Aldrich) at −78° C. under argon. After 30 minutes, a solution of 4-methoxyphenylacetic acid methyl ester (900 mg, 5.0 mmol) (Aldrich) in tetrahydrofuran (3 mL) was added by injection via a syringe and the reaction mixture was stirred at −78° C. for another 30 minutes. To this reaction mixture was added a solution of 2,4-dichloro-5-iodomethyl-pyrimidine (722. 5 mg, 2.5 mmol) (from Example 1c supra) in tetrahydrofuran (3 mL) at −78° C. and the reaction mixture was stirred at the same temperature for 1 hour, then slowly allowed to warm up to −30° C. and stirred for 10 minutes. The reaction mixture was diluted with ethyl acetate (100 mL) and successively washed with saturated aqueous ammonium chloride solution (50 mL), water (30 mL), and brine (30 mL), dried over anhydrous sodium sulfate, filtered, and concentrated in vacuo. The residue was purified by flash column chromatography to give 3-(2,4-dichloro-pyrimidin-5-yl)-2-(4-methoxy-phenyl)-propionic acid methyl ester as a yellow oil. (Yield 620 mg, 72.7%).

Example 1e 3-(2,4-Diphenylamino-pyrimidin-5-yl)-2-(4-methoxy-phenyl)-propionic acid methyl ester

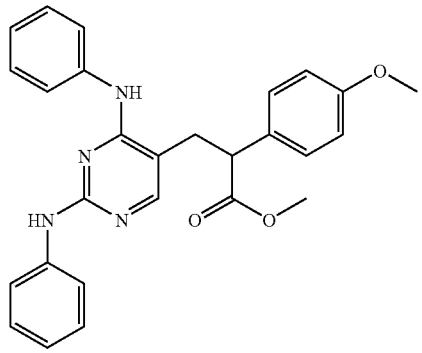

A mixture of 3-(2,4-dichloro-pyrimidin-5-yl)-2-(4-methoxy-phenyl)-propionic acid methyl ester (0.54 g, 1.58 mmol) (from Example 1d supra) and aniline (0.67 g, 7.11 mmol) (Aldrich) was heated at 110° C. for 30 minutes. The reaction mixture was washed with hexanes (50 mL×3) and the supernatant was decanted off after each time. The residue was then dissolved in ethyl acetate (100 mL) and successively washed with saturated aqueous ammonium chloride solution (30 mL), water (30 mL) and brine (30 mL), dried over anhydrous sodium sulfate, filtered, and concentrated in vacuo. The crude products was purified by flash column chromatography (silica gel) to give 3-(2,4-diphenylamino-pyrimidin-5-yl)-2-(4-methoxy-phenyl)-propionic acid methyl ester as a white amorphous solid. (Yield 0.49 g, 68.1%).

Example 1f 6-(4-Methoxy-phenyl)-8-phenyl-2-phenylamino-5,8-dihydro-6H-pyrido[2,3-d]pyrimidin-7-one

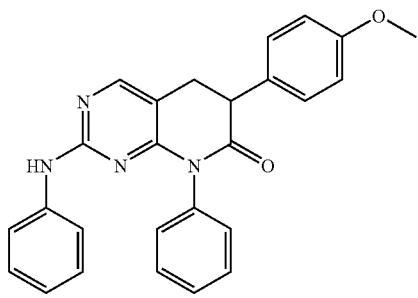

To the solution of 3-(2,4-diphenylamino-pyrimidin-5-yl)-2-(4-methoxy-phenyl)-propionic acid methyl ester (227.3 mg, 0.5 mmol) (from Example 1e supra) in glacial acetic acid (15 mL) was added concentrated sulfuric acid (0.2 mL) in one portion. The reaction mixture was heated at 80° C. overnight. The reaction mixture was then diluted with ethyl acetate (50 mL) and quenched with 2 N aqueous sodium hydroxide solution. The organic layer was separated and successively washed with water (10 mL) and brine (10 mL), dried over anhydrous sodium sulfate, filtered, and concentrated in vacuo to give the crude products which was crystallized from ethyl acetate-hexanes to give 6-(4-methoxy-phenyl)-8-phenyl-2-phenylamino-5,8-dihydro-6H-pyrido[2,3-d]pyrimidin-7-one as brown crystalline solid. (Yield 174.2 mg, 82.4%).

HRMS m/z Calcd for $C_{26}H_{22}N_4O_2$ [(M+H)$^+$]: 423.1816. Found: 423.1817.

Example 2a 2-(2,6-Dichloro-phenyl)-3-(2,4-dichloro-pyrimidin-5-yl)-propionic acid methyl ester

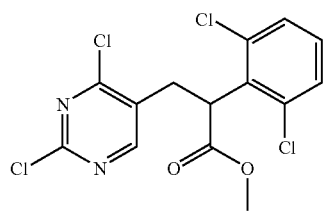

To a solution of N-isopropylcyclohexylamine (1.44 g, 10.0 mmol) (Aldrich) in dry tetrahydrofuran (20 mL) was added n-butyllithium (2.5 M in hexanes, 4.0 mL, 10.0 mmol) (Aldrich) at −78° C. under argon. After 30 minutes, a solution of 2,6-dichloro-phenylacetic acid methyl ester (2.19 g, 10.0 mmol) (TCI-US) in tetrahydrofuran (5 mL) was added by injection via a syringe and the reaction mixture was stirred at −78° C. for another 30 minutes. To this reaction mixture was added a solution of 2,4-dichloro-5-iodomethyl-pyrimidine (1.45 g, 5.0 mmol) (from Example 1c supra) in tetrahydrofuran (5 mL) at −78° C. and the reaction mixture was stirred at the same temperature for 1 hour then slowly allowed to warm up to −30° C. and stirred for 10 minutes. The reaction mixture was diluted with ethyl acetate (100 mL) and successively washed with saturated aqueous ammonium chloride solution (100 mL), water (50 mL) and brine (50 mL), dried over anhydrous sodium sulfate, filtered, and concentrated in vacuo. The residue was purified by flash column chromatography to give 2-(2,6-dichloro-phenyl)-3-(2,4-dichloro-pyrimidin-5-yl)-propionic acid methyl ester as a colorless oil. (Yield 1.57 g, 82.6%).

Example 2b 3-(2,4-Diphenylamino-pyrimidin-5-yl)-2-(2,6-Dichloro-phenyl)-propionic acid methyl ester

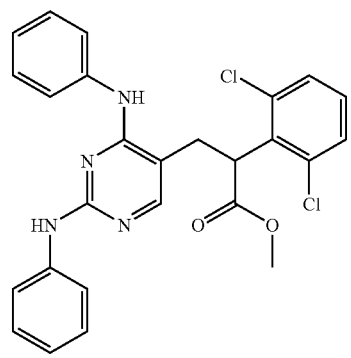

A mixture of 2-(2,6-dichloro-phenyl)-3-(2,4-dichloro-pyrimidin-5-yl)-propionic acid methyl ester (0.20 g, 0.53 mmol) (from Example 2a supra) and aniline (2.0 ml) (Aldrich) was heated at 110° C. for 2 hours. The reaction mixture was washed with hexanes (50 mL×3) and the supernatant was decanted off after each time. The residue was then dissolved in ethyl acetate (100 mL) and successively washed with saturated aqueous ammonium chloride solution (30 mL), water (30 mL) and brine (30 mL), dried over anhydrous sodium sulfate, filtered, and concentrated in vacuo to give the crude 3-(2,4-diphenylamino-pyrimidin-5-yl)-2-(2,6-dichloro-phenyl)-propionic acid methyl ester as a brown caramel which was used in the next step without further purification. (Yield 0.18 g, 69.3%).

Example 2c 6-(2,6-Dichloro-phenyl)-8-phenyl-2-phenylamino-5,8-dihydro-6H-pyrido[2,3-d]pyrimidin-7-one

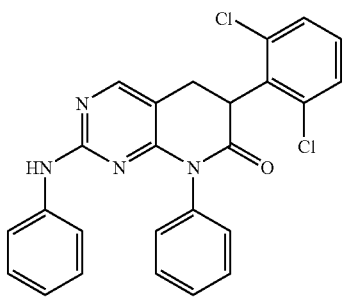

To a solution of 3-(2,4-diphenylamino-pyrimidin-5-yl)-2-(2,6-dichloro-phenyl)-propionic acid methyl ester (0.18 g, 0.36 mmol) (from Example 2b supra) in glacial acetic acid (2 mL) was added concentrated sulfuric acid (0.1 mL) in one portion. The reaction mixture was heated at 135° C. overnight and 145° C. for another 4 hours. After cooling, the reaction mixture was diluted with ethyl acetate (50 mL) and quenched with 2 N aqueous sodium hydroxide solution. The organic layer was separated and successively washed with water (10 mL) and brine (10 mL), dried over anhydrous sodium sulfate, filtered, and concentrated in vacuo to give the crude product which was crystallized from ethyl acetate-hexanes to give 6-(2,6-dichloro-phenyl)-8-phenyl-2-phenylamino-5,8-dihydro-6H-pyrido[2,3-d]pyrimidin-7-one as a gray solid. (Yield 61.2 mg, 36.3%).

HRMS m/z Calcd for $C_{25}H_{18}Cl_2N_4O$ (M+): 461.0931. Found: 461.0934.

Example 3a 3,5-Dimethoxyphenylacetic acid methyl ester

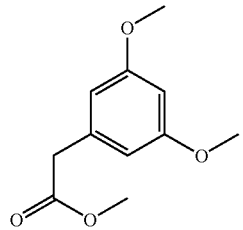

To a solution of 3,5-dimethoxyphenylacetic acid (1.99 g, 10.0 mmol) (Transworld) in methanol (20 mL) was added concentrated sulfuric acid (1.0 mL) and the reaction mixture was heated at reflux for 24 hours. The reaction mixture was concentrated in vacuo. The residue was then diluted with ethyl acetate (100 mL) and successively washed with water (50 mL) and brine (50 mL), dried over anhydrous sodium sulfate, filtered, and concentrated in vacuo to give the crude 3,5-dimethoxyphenylacetic acid methyl ester as a black oil which was used in the next step without further purification. (Yield 2.05 g, 97.6%).

Example 3b 3-(2,4-Dichloro-pyrimidin-5-yl)-2-(3,5-dimethoxy-phenyl)-propionic acid methyl ester

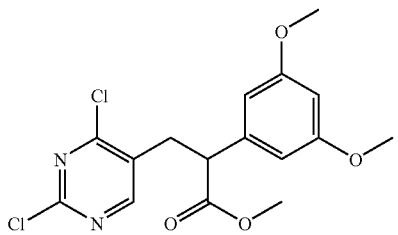

To a solution of N-isopropylcyclohexylamine (1.44 g, 10.0 mmol) (Aldrich) in dry tetrahydrofuran (20 mL) was added n-butyllithium (2.5 M in hexanes, 4.0 mL, 10.0 mmol) (Aldrich) at −78° C. under argon. After 30 minutes, a solution of 3,5-dimethoxy-phenyl-acetic acid methyl ester (2.05 g, 9.76 mmol) (from Example 3a supra) in tetrahydrofuran (5 mL) was added by injection via a syringe and the reaction mixture was stirred at −78° C. for another 30 minutes. To this reaction mixture was added a solution of 2,4-dichloro-5-iodomethyl-pyrimidine (1.45 g, 5.0 mmol) (from Example 1c supra) in tetrahydrofuran (5 mL) at −78° C. and the reaction mixture was stirred at the same temperature for 1 hour then slowly allowed to warm up to −30° C. and stirred for 10 minutes. The reaction mixture was diluted with ethyl acetate (100 mL) and successively washed with saturated aqueous ammonium chloride solution (100 mL), water (50 mL) and brine (50 mL), dried over anhydrous sodium sulfate, filtered, and concentrated in vacuo. The residue was purified by flash column chromatography to give 3-(2,4-dichloro-pyrimidin-5-yl)-2-(3,5-dimethoxy-phenyl)-propionic acid methyl ester as a colorless oil. (Yield 1.45 g, 78.0%).

Example 3c 3-(2,4-Diphenylamino-pyrimidin-5-yl)-2-(3,5-dimethoxy-phenyl)-propionic acid methyl ester

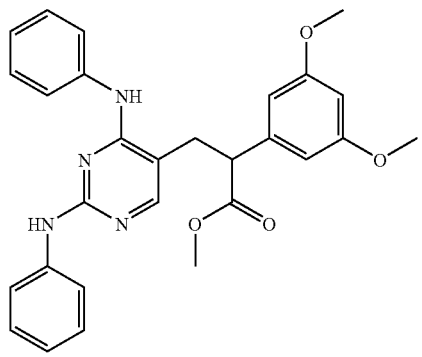

A mixture of 3-(2,4-dichloro-pyrimidin-5-yl)-2-(3,5-dimethoxy-phenyl)-propionic acid methyl ester (186 mg, 0.50 mmol) (from Example 3b supra) and aniline (2.0 mL) (Aldrich) was heated at 110° C. for 2 hours. The reaction mixture was washed with hexanes (50 mL×3) and the supernatant was decanted off after each time. The residue was dissolved in ethyl acetate (100 mL) and successively washed with saturated aqueous ammonium chloride solution (30 mL), water (30 mL) and brine (30 mL), dried over anhydrous sodium sulfate, filtered, and concentrated in vacuo to give the crude 3-(2,4-diphenylamino-pyrimidin-5-yl)-2-(3,5-dimethoxy-phenyl)-propionic acid methyl ester as an off-white solid which was used in the next step without further purification. (Yield 241.5 mg, 99.7%).

Example 3d 6-(3,5-Dimethoxy-phenyl)-8-phenyl-2-phenylamino-5,8-dihydro-6H-pyrido[2,3-d]pyrimidin-7-one

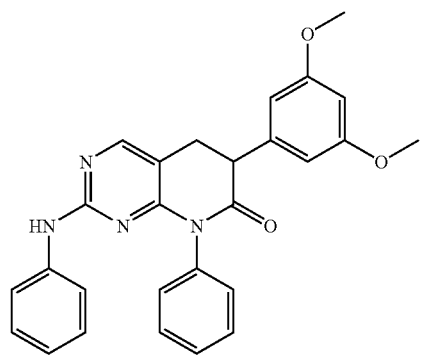

To a solution of 3-(2,4-diphenylamino-pyrimidin-5-yl)-2-(3,5-dimethoxy-phenyl)-propionic acid methyl ester (0.11 mg, 0.23 mmol) (from Example 3c supra) in glacial acetic acid (2 mL) was added concentrated sulfuric acid (0.1 mL) in one portion. The reaction mixture was heated at 120° C. overnight. The reaction mixture was then diluted with ethyl acetate (50 mL) and quenched with 2 N aqueous sodium hydroxide solution. The organic layer was separated and successively washed with water (10 mL) and brine (10 mL), dried over anhydrous sodium sulfate, filtered, and concentrated in vacuo to give the crude product which was crystallized from ethyl acetate-hexanes to give 6-(3,5-dimethoxy-phenyl)-8-phenyl-2-phenylamino-5,8-dihydro-6H-pyrido[2,3-d]pyrimidin-7-one as light brown solid. (Yield 73.3 mg, 71.4%).

HRMS m/z Calcd for $C_{27}H_{24}N_4O_3$ [(M+H)$^+$]: 453.1921. Found: 453.1926.

Example 4a 3-(2,4-Dichloro-pyrimidin-5-yl)-2-O-tolyl-propionic acid methyl ester

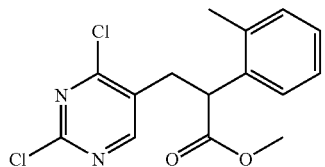

To a solution of N-isopropylcyclohexylamine (1.44 g, 10.0 mmol) (Aldrich) in dry tetrahydrofuran (20 mL) was added n-butyllithium (2.5 M in hexanes, 4.0 mL, 10.0 mmol) (Aldrich) at −78° C. under argon. After 30 minutes, a solution of O-tolyl-acetic acid methyl ester (1.64 g, 10.0 mmol) (Lancaster) in tetrahydrofuran (5 mL) was added by injection via a syringe and the reaction mixture was stirred at −78° C. for another 30 minutes. To this reaction mixture was added a solution of 2,4-dichloro-5-iodomethyl-pyrimidine (1.45 g, 5.0 mmol) (from Example 1c supra) in tetrahydrofuran (5 mL) at −78° C. and the reaction mixture was stirred at the same temperature for 1 hour then slowly allowed to warm up to −30° C. and stirred for 10 minutes. The reaction mixture was diluted with ethyl acetate (100 mL) and successively washed with saturated aqueous ammonium chloride solution (100 mL), water (50 mL) and brine (50 mL), dried over anhydrous sodium sulfate, filtered, and concentrated in vacuo. The residue was purified by flash column chromatography to give 3-(2,4-dichloro-pyrimidin-5-yl)-2-O-tolyl-propionic acid methyl ester as a colorless oil. (Yield 1.25 g, 77.2%).

Example 4b 3-(2,4-Diphenylamino-pyrimidin-5-yl)-2-O-tolyl-propionic acid methyl ester

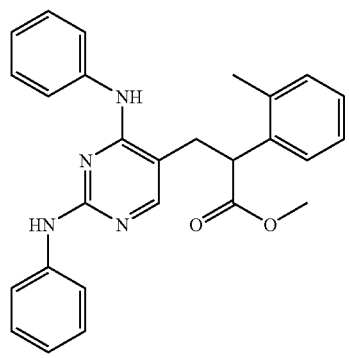

A mixture of 3-(2,4-dichloro-pyrimidin-5-yl)-2-O-tolyl-propionic acid methyl ester (0.28 g, 0.86 mmol) (from Example 4a supra) and aniline (2.0 mL) (Aldrich) was heated at 120° C. for 1 hour. The reaction mixture was washed with hexanes (50 mL×3) and the supernatant was decanted off after each time. The resulting solid was collected by filtration and washed with diethyl ether to give the crude 3-(2,4-diphenylamino-pyrimidin-5-yl)-2-O-tolyl-propionic acid methyl ester as a white solid which was used in the next step without further purification. (Yield 412 mg).

Example 4c

8-Phenyl-2-phenylamino-6-O-tolyl-5,8-dihydro-6H-pyrido[2,3-d]pyrimidin-7-one

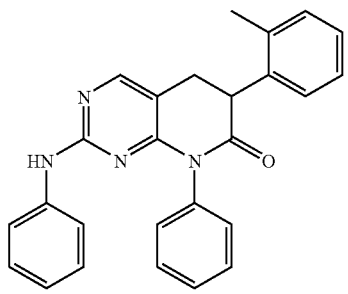

To a solution of 3-(2,4-diphenylamino-pyrimidin-5-yl)-2-O-tolyl-propionic acid methyl ester (170 mg, 0.39 mmol) (from Example 4b supra) in glacial acetic acid (3 mL) added concentrated sulfuric acid (0.2 mL) in one portion. The reaction mixture was heated at 110° C. overnight. The reaction mixture was then diluted with ethyl acetate (50 mL) and quenched with 2 N aqueous sodium hydroxide solution. The organic layer was separated and successively washed with water (10 mL) and brine (10 mL), dried over anhydrous sodium sulfate, filtered, and concentrated in vacuo to give the crude products which was crystallized from ethyl acetate-hexanes to give 8-phenyl-2-phenylamino-6-O-tolyl-5,8-dihydro-6H-pyrido[2,3-d]pyrimidin-7-one as a white solid. (Yield 122.6 mg, 77.7%).

HRMS m/z Calcd for $C_{26}H_{22}N_4O$ [(M+H)$^+$]: 407.1867. Found: 407.1866.

Example 5a 3-(2,4-Dichloro-pyrimidin-5-yl)-2-phenyl-propionic acid methyl ester

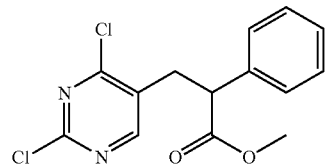

To a solution of N-isopropylcyclohexylamine (1.44 g, 10.0 mmol) (Aldrich) in dry tetrahydrofuran (20 mL) was added n-butyllithium (2.5 M in hexanes, 4.0 mL, 10.0 mmol) (Aldrich) at −78° C. under argon. After 30 minutes, a solution of phenylacetic acid methyl ester (1.50 g, 10.0 mmol) (Aldrich) in tetrahydrofuran (5 mL) was added by injection via a syringe and the reaction mixture was stirred at −78° C. for another 30 minutes. To the reaction mixture was added a solution of 2,4-dichloro-5-iodomethyl-pyrimidine (1.45 g, 5.0 mmol) (from Example 1c supra) in tetrahydrofuran (5 mL) at −78° C. and the reaction mixture was stirred at the same temperature for 1 hour then slowly allowed to warm up to −30° C. and stirred for 10 minutes. The reaction mixture was diluted with ethyl acetate (100 mL) and successively washed with saturated aqueous ammonium chloride solution (100 mL), water (50 mL) and brine (50 mL), dried over anhydrous sodium sulfate, filtered, and concentrated in vacuo. The residue was purified by flash column chromatography to give 3-(2,4-dichloro-pyrimidin-5-yl)-2-phenyl-propionic acid methyl ester as a colorless oil. (Yield 1.00 g, 64.5%).

Example 5b 3-(2,4-Diphenylamino-pyrimidin-5-yl)-2-phenyl-propionic acid methyl ester

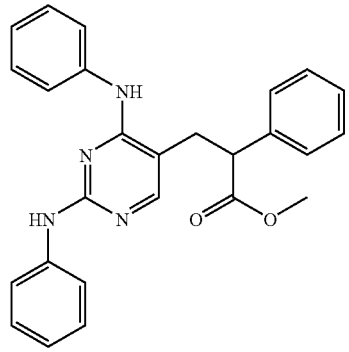

The mixture of 3-(2,4-dichloro-pyrimidin-5-yl)-2-phenyl-propionic acid methyl ester (0.31 g, 1.0 mmol) (from Example 5a supra) and aniline (3.0 mL) (Aldrich) was heated at 120° C. for 1 hour. The reaction mixture was washed with hexanes (50 mL×3) and the supernatant was decanted off after each time. The residue was then dissolved in ethyl acetate (100 mL) and successively washed with saturated aqueous ammonium chloride solution (30 mL), water (30 mL) and brine (30 mL), dried over anhydrous sodium sulfate, filtered, and concentrated in vacuo. The crude product was purified by flash column chromatography (silica gel) to give 3-(2,4-diphenylamino-pyrimidin-5-yl)-2-phenyl-propionic acid methyl ester as a white amorphous solid. (Yield 0.35 g, 82.3%).

Example 5c 6,8-Diphenyl-2-phenylamino-5,8-dihydro-6H-pyrido[2,3-d]pyrimidin-7-one

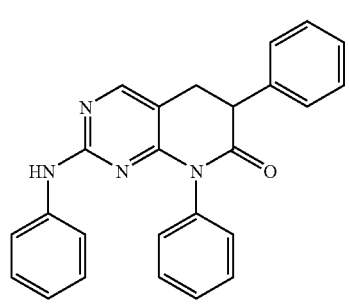

To a solution of 3-(2,4-diphenylamino-pyrimidin-5-yl)-2-phenyl-propionic acid methyl ester (100 mg, 0.24 mmol) (from Example 5b supra) was added 5% concentrated sulfuric acid in glacial acetic acid (3 mL) in one portion. The reaction mixture was heated at 60° C. overnight. After cooling, the reaction mixture was diluted with ethyl acetate (50 mL) and quenched with 2 N aqueous sodium hydroxide solution. The organic layer was separated and successively washed with water (10 mL) and brine (10 mL), dried over anhydrous sodium sulfate, filtered, and concentrated in vacuo to give the crude product which was crystallized from ethyl acetate-hexanes to give 6,8-diphenyl-2-phenylamino-5,8-dihydro-6H-pyrido[2,3-d]pyrimidin-7-one as a light brown solid. (Yield 61.2 mg, 66.2%). HRMS m/z Calcd for $C_{25}H_{20}N_4O$ [(M+H)$^+$]: 393.1710. Found: 393.1714.

Example 6a 3-(2,4-Dichloro-pyrimidin-5-yl)-2-(2,5-dimethoxy-phenyl)-propionic acid ethyl ester

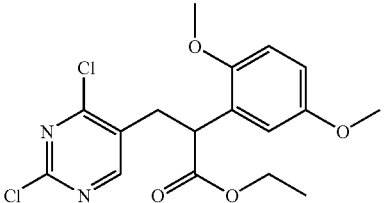

To a solution of N-isopropylcyclohexylamine (1.44 g, 10.0 mmol) (Aldrich) in dry tetrahydrofuran (20 mL) was added n-butyllithium (2.5 M in hexanes, 4.0 mL, 10.0 mmol) (Aldrich) at −78° C. under argon. After 30 minutes, a solution of 2,5-dimethoxyphenylacetic acid ethyl ester (2.24 g, 10.0 mmol) (Aldrich) in tetrahydrofuran (5 mL) was added by injection via a syringe and the reaction mixture was stirred at −78° C. for another 30 minutes. To the reaction mixture was added a solution of 2,4-dichloro-5-iodomethyl-pyrimidine (1.45 g, 5.0 mmol) (from Example 1c supra) in tetrahydrofuran (5 mL) at −78° C. and the reaction mixture was stirred at the same temperature for 1 hour then slowly allowed to warm up to −30° C. and stirred for 10 minutes. The reaction mixture was diluted with ethyl acetate (100 mL) and successively washed with saturated aqueous ammonium chloride solution (100 mL), water (50 mL) and brine (50 mL), dried over anhydrous sodium sulfate, filtered, and concentrated in vacuo. The residue was purified by flash column chromatography to give 3-(2,4-dichloro-pyrimidin-5-yl)-2-(2,5-dimethoxy-phenyl)-propionic acid ethyl ester as a colorless oil. (Yield 1.00 g, 51.9%).

Example 6b 3-(2,4-Diphenylamino-pyrimidin-5-yl)-2-(2,5-dimethoxy-phenyl propionic acid ethyl ester

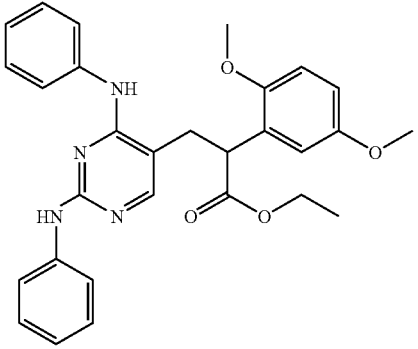

The mixture of 3-(2,4-dichloro-pyrimidin-5-yl)-2-(2,5-dimethoxy-phenyl)-propionic acid ethyl ester (0.36 g, 0.94 mmol) (from Example 6a supra) and aniline (2.0 mL)

(Aldrich) was heated at 120° C. for 2 hours. The reaction mixture was washed with hexanes (50 mL×3), and the supernatant was decanted off after each time. The residue was dissolved in ethyl acetate (100 mL) and successively washed with saturated aqueous ammonium chloride solution (30 mL), water (30 mL) and brine (30 mL), dried over anhydrous sodium sulfate, filtered, and concentrated in vacuo. The crude product was triturated with ethyl acetate-hexanes. The resulting solid was collected by filtration and washed with diethyl ether to give 3-(2,4-diphenylamino-pyrimidin-5-yl)-2-(2,5-dimethoxy-phenyl propionic acid ethyl ester as a yellow solid, which was used in the next step without further purification. (Yield 437.6 mg, 93.9%).

Example 6c 6-(2,5-Dimethoxy-phenyl)-8-phenyl-2-phenylamino-5,8-dihydro-6H-pyrido[2,3-d]pyrimidin-7-one

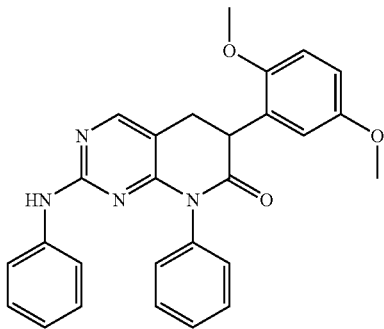

To a solution of 3-(2,4-diphenylamino-pyrimidin-5-yl)-2-(2,5-dimethoxy-phenyl propionic acid ethyl ester (100 mg, 0.20 mmol) (from Example 6b supra) was added 5% concentrated sulfuric acid in glacial acetic acid (2 mL) in one portion. The reaction mixture was heated at 110° C. for 2.5 hours. The reaction mixture was then diluted with ethyl acetate (50 mL) and quenched with 2 N aqueous sodium hydroxide solution. The organic layer was separated and successively washed with water (10 mL) and brine (10 mL), dried over anhydrous sodium sulfate, filtered, and concentrated in vacuo to give the crude product which was crystallized from ethyl acetate-hexanes to give 6-(2,5-Dimethoxy-phenyl)-8-phenyl-2-phenylamino-5,8-dihydro-6H-pyrido[2,3-d]pyrimidin-7-one as an off-white solid. (Yield 75.6 mg, 83.5%).

HRMS m/z Calcd for $C_{27}H_{24}N_4O_3$ [(M+H)$^+$]: 453.1921. Found: 453.1925.

Example 7a 3-(2,4-Dichloro-pyrimidin-5-yl)-2-(2-methoxy-phenyl)-propionic acid methyl ester

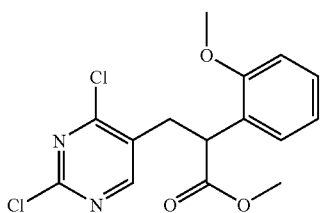

To a solution of N-isopropylcyclohexylamine (1.44 g, 10.0 mmol) (Aldrich) in dry tetrahydrofuran (20 mL) was added n-butyllithium (2.5 M in hexanes, 4.0 mL, 10.0 mmol) (Aldrich) at −78° C. under argon. After 30 minutes, a solution of 2-methoxyphenylacetic acid methyl ester (1.8 g, 10.0 mmol) (TCI-US) in tetrahydrofuran (5 mL) was added by injection via a syringe and the reaction mixture was stirred at −78° C. for another 30 minutes. To the reaction mixture was added a solution of 2,4-dichloro-5-iodomethyl-pyrimidine (1.45 g, 5.0 mmol) (from Example 1c supra) in tetrahydrofuran (5 mL) at −78° C. and the reaction mixture was stirred at the same temperature for 1 hour then slowly allowed to warm up to −30° C. and stirred for 10 minutes. The reaction mixture was diluted with ethyl acetate (100 mL) and successively washed with saturated aqueous ammonium chloride solution (100 mL), water (50 mL) and brine (50 mL), dried over anhydrous sodium sulfate, filtered, and concentrated in vacuo. The residue was purified by flash column chromatography to give 3-(2,4-dichloro-pyrimidin-5-yl)-2-(2-methoxy-phenyl)-propionic acid methyl ester as a yellow oil. (Yield 1.40 g, 82.3%).

Example 7b 3-(2,4-Diphenylamino-pyrimidin-5-yl)-2-(2-methoxy-phenyl) propionic acid ethyl ester

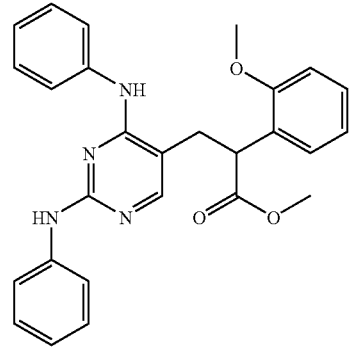

A mixture of 3-(2,4-dichloro-pyrimidin-5-yl)-2-(2-methoxy-phenyl)-propionic acid methyl ester (0.34 g, 1.0 mmol) (from Example 7a supra) and aniline (2.0 mL) (Aldrich) was heated at 120° C. for 1 hour. The reaction mixture was washed with hexanes (50 mL×3) and the supernatant was decanted off after each time. The residue was dissolved in ethyl acetate (100 mL) and successively washed with saturated aqueous ammonium chloride solution (30 mL), water (30 mL) and brine (30 mL), dried over anhydrous sodium sulfate, filtered, and concentrated in vacuo. The crude product was triturated with ethyl acetate-hexanes. The resulting solid was collected by filtration and washed with diethyl ether to give 3-(2,4-diphenylamino-pyrimidin-5-yl)-2-(2-methoxy-phenyl) propionic acid methyl ester as a yellow solid which was used in the next step without further purification. (Yield 340.0 mg, 74.9%).

Example 7c 6-(2-Methoxy-phenyl)-8-phenyl-2-phenylamino-5,8-dihydro-6H-pyrido[2,3-d]pyrimidin-7-one

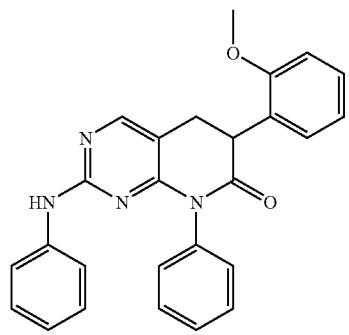

To a solution of 3-(2,4-diphenylamino-pyrimidin-5-yl)-2-(2-dimethoxy-phenyl propionic acid methyl ester (181.8 mg, 0.40 mmol) (from Example 7b supra) was added 5% concentrated sulfuric acid in glacial acetic acid (3 mL) in one portion. The reaction mixture was heated at 110° C. for 3 hours. After cooling, the reaction mixture was diluted with ethyl acetate (100 mL) and quenched with 2 N aqueous sodium hydroxide solution. The organic layer was separated and successively washed with water (30 mL) and brine (30 mL), dried over anhydrous sodium sulfate, filtered, and concentrated in vacuo to give the crude product. The crude product was crystallized from ethyl acetate-hexanes to give 6-(2-methoxy-phenyl)-8-phenyl-2-phenylamino-5,8-dihydro-6H-pyrido[2,3-d]pyrimidin-7-one as an off-white solid. (Yield 119.4 mg, 67.2%).

HRMS m/z Calcd for $C_{26}H_{22}N_4O_2$ (M+): 422.1743. Found: 422.1747.

Example 8a 3,5-Bis-trifluoromethylphenylacetic acid methyl ester

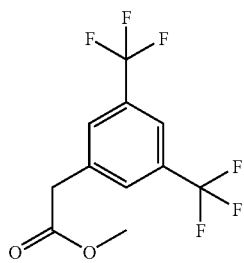

To a solution of 3,5-bis-trifluoromethylphenylacetic acid (3.0 g, 11.03 mmol) (Aldrich) in methanol (20 mL) was added concentrated sulfuric acid (1.0 mL) and the reaction mixture was heated at reflux overnight. The reaction mixture was concentrated in vacuo. The residue was then diluted with ethyl acetate (100 mL) and successively washed with water (50 mL) and brine (50 mL), dried over anhydrous sodium sulfate, filtered, and concentrated in vacuo. The crude material was purified by flash column chromatography to give 3,5-bis-trifluoromethylphenylacetic acid methyl ester as a colorless oil. (Yield 2.27 g, 72.1%).

Example 8b 2-(3,5-Bis-trifluoromethyl-phenyl)-3-(2,4-dichloro-pyrimidin-5-yl)-propionic acid methyl ester

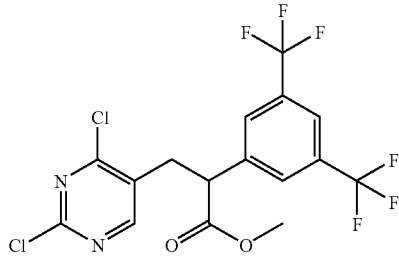

To a solution of N-isopropylcyclohexylamine (1.44 g, 10.0 mmol) (Aldrich) in dry tetrahydrofuran (20 mL) was added n-butyllithium (2.5 M in hexanes, 4.0 mL, 10.0 mmol) (Aldrich) at −78° C. under argon. After 10 minutes, a solution of 3,5-bis-trifluoromethylphenylacetic acid methyl ester (2.20 g, 7.7 mmol) (from Example 8a supra) in tetrahydrofuran (5 mL) was added by injection via a syringe and the reaction mixture was stirred at −78° C. for another 10 minutes. To the reaction mixture was added a solution of 2,4-dichloro-5-iodomethyl-pyrimidine (1.45 g, 5.0 mmol) (from Example 1c supra) in tetrahydrofuran (5 mL) at −78° C. and the reaction mixture was stirred at the same temperature for 2 hours then slowly allowed to warm up to −20° C. and stirred for 10 minutes. The reaction mixture was diluted with ethyl acetate (100 mL) and successively washed with saturated aqueous ammonium chloride solution (100 mL), water (50 mL) and brine (50 mL), dried over anhydrous sodium sulfate, filtered, and concentrated in vacuo. The residue was purified by flash column chromatography to give 2-(3,5-bis-trifluoromethyl-phenyl)-3-(2,4-dichloro-pyrimidin-5-yl)-propionic acid methyl ester as a colorless oil. (Yield 1.71 g, 76.5%).

Example 8c 3-(2,4-Diphenylamino-pyrimidin-5-yl)-2-(3,5-bis-trifluoromethyl-phenyl)-propionic acid methyl ester

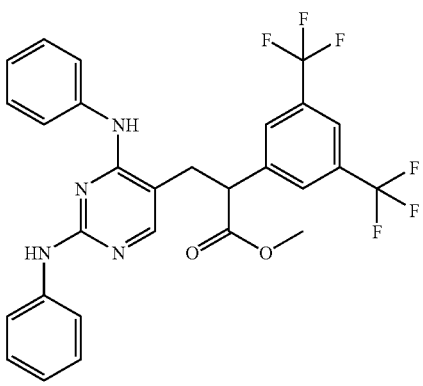

A mixture of 2-(3,5-bis-trifluoromethyl-phenyl)-3-(2,4-dichloro-pyrimidin-5-yl)-propionic acid methyl ester (0.35 g, 0.78 mmol) (from Example 8b supra) and aniline (2.0 mL) (Aldrich) was heated at 120° C. for 1 hour. The reaction mixture was washed with hexanes (50 mL×3) and the supernatant was decanted off after each time. The residue was dissolved in ethyl acetate (100 mL) and successively washed with saturated aqueous ammonium chloride solution (30 mL), water (30 mL) and brine (30 mL), dried over anhydrous sodium sulfate, filtered, and concentrated in vacuo. The crude product was then triturated with ethyl acetate-hexanes. The resulting solid was collected by filtration and washed with diethyl ether to give crude 3-(2,4-diphenylamino-pyrimidin-5-yl)-2-(3,5-bis-trifluoromethyl-phenyl)-propionic acid methyl ester as an off-white solid which was used in the next step without further purification. (Yield 0.47 g).

Example 8d 6-(3,5-Bis-triflouromethyl-phenyl)-8-phenyl-2-phenylamino-5,8-dihydro-6H-pyrido[2,3-d]pyrimidin-7-one

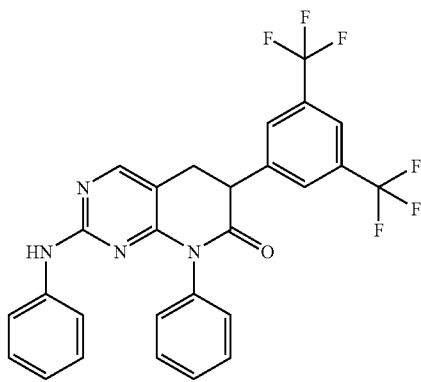

To a solution of 3-(2,4-diphenylamino-pyrimidin-5-yl)-2-(3,5-bis-trifluoromethyl-phenyl)-propionic acid methyl ester (0.20 g, 0.36 mmol) (from Example 8c supra) was added 5% concentrated sulfuric acid in glacial acetic acid (3 mL) in one portion. The reaction mixture was heated at 120° C. for 3 hours. The reaction mixture was then diluted with ethyl acetate (100 mL) and quenched with 2 N aqueous sodium hydroxide solution. The organic layer was separated and successively washed with water (30 mL) and brine (30 mL), dried over anhydrous sodium sulfate, filtered, and concentrated in vacuo to give the crude product which was crystallized from ethyl acetate-hexanes to give 6-(3,5-bis-trifluoromethyl-phenyl)-8-phenyl-2-phenylamino-5,8-dihydro-6H-pyrido[2,3-d]pyrimidin-7-one as an off-white solid. (Yield 130.3 mg, 70.5%).

HRMS m/z Calcd for $C_{27}H_{18}F_6N_4O$ [(M+H)$^+$]: 529.1458. Found: 529.1464.

Example 9a 3-(2,4-Dichloro-pyrimidin-5-yl)-2-pyridin-4-yl-propionic acid ethyl ester

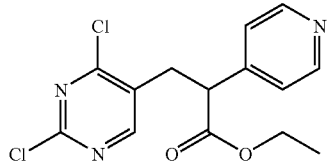

To a solution of N-isopropylcyclohexylamine (720 mg, 5.0 mmol) (Aldrich) in dry tetrahydrofuran (10 mL) was added n-butyllithium (2.5 M in hexanes, 2.0 mL, 5.0 mmol) (Aldrich) at −78° C. under argon. After 30 minutes, a solution of 4-pyridylacetic acid ethyl ester (826 mg, 5.0 mmol) (Lancaster) in tetrahydrofuran (3 mL) was added by injection via a syringe and the reaction mixture was stirred at −78° C. for another 30 minutes. To the reaction mixture was added a solution of 2,4-dichloro-5-iodomethyl-pyrimidine (722.5 mg, 2.5 mmol) (from Example 1c supra) in tetrahydrofuran (3 mL) at −78° C. and the reaction mixture was stirred at the same temperature for 1 hour then slowly allowed to warm up to −30° C. and stirred for 10 minutes. The reaction mixture was diluted with ethyl acetate (100 mL) and successively washed with saturated aqueous ammonium chloride solution (50 mL), water (30 mL) and brine (30 mL), dried over anhydrous sodium sulfate, filtered, and concentrated in vacuo to give the crude 3-(2,4-dichloro-pyrimidin-5-yl)-2-pyridin-4-yl-propionic acid ethyl ester which was used in the next step without further purification. (Yield 1.43 g, 83.6%).

Example 9b 3-(2,4-Diphenylamino-pyrimidin-5-yl)-2-pyridin-4-yl-propionic acid ethyl ester

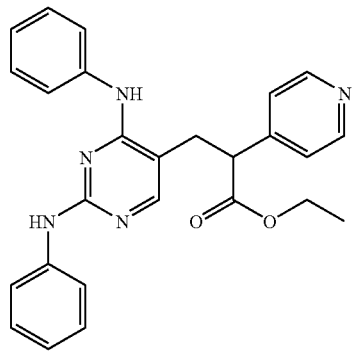

A mixture of 3-(2,4-dichloro-pyrimidin-5-yl)-2-pyridin-4-yl-propionic acid ethyl ester (0.68 g, 2.0 mmol) (from Example 9a supra) and aniline (3.0 mL) (Aldrich) was heated at 120° C. for 2 hours. The reaction mixture was washed with hexanes (50 mL×3) and the supernatant was decanted off after each time. The residue was then dissolved in ethyl acetate (100 mL) and successively washed with saturated aqueous ammonium chloride solution (30 mL), water (30 mL) and brine (30 mL), dried over anhydrous sodium sulfate, filtered, and concentrated in vacuo. The crude product was triturated with ethyl acetate-hexanes. The resulting solid was collected by filtration and washed with diethyl ether to give 3-(2,4-diphenylamino-pyrimidin-5-yl)-2-pyridin-4-yl-propionic acid ethyl ester as a brown solid which was used in the next step without further purification. (Yield 0.54 g, 83.1%).

Example 9c

8-Phenyl-2-phenylamino-6-pyridin-4-yl-5,8-dihydro-6H-pyrido[2,3-d]pyrimidin-7-one

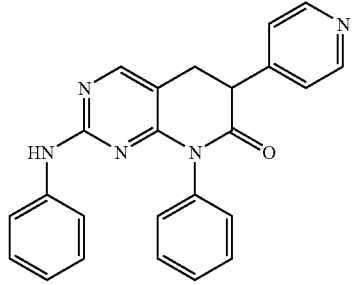

To a solution of 3-(2,4-diphenylamino-pyrimidin-5-yl)-2-pyridin-4-yl-propionic acid ethyl ester (200 mg, 0.46 mmol) (from Example 9b supra) was added 5% concentrated sulfuric acid in glacial acetic acid (3 mL) in one portion. The reaction mixture was heated at 80° C. overnight. The reaction mixture was then diluted with ethyl acetate (100 mL) and quenched with 2 N aqueous sodium hydroxide solution. The organic layer was separated and successively washed with water (30 mL) and brine (30 mL), dried over anhydrous sodium sulfate, filtered, and concentrated in vacuo to give the crude product which was crystallized from ethyl acetate-hexanes to give 8-phenyl-2-phenylamino-6-pyridin-4-yl-5,8-dihydro-6H-pyrido[2,3-d]pyrimidin-7-one as a yellow solid. (Yield 140 mg, 78.2%).

HRMS m/z Calcd for $C_{24}H_{19}N_5O$ [(M+H)$^+$]: 394.1663. Found: 394.1662.

Example 10a 3-(2,4-Dichloro-pyrimidin-5-yl)-2-pyridin-3-yl-propionic acid ethyl ester

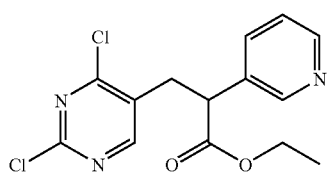

To a solution of N-isopropylcyclohexylamine (1.44 g, 10.0 mmol) (Aldrich) in dry tetrahydrofuran (20 mL) was added n-butyllithium (2.5 M in hexanes, 4.0 mL, 10.0 mmol) (Aldrich) at −78° C. under argon. After 10 minutes, a solution of 2-pyridin-3-yl-acetic acid ethyl ester (1.65 g, 10.0 mmol) (Acros) in tetrahydrofuran (5 mL) was added by injection via a syringe and the reaction mixture was stirred at −78° C. for another 10 minutes. To the reaction mixture was added a solution of 2,4-dichloro-5-iodomethyl-pyrimidine (1.45 g, 5.0 mmol) (from Example 1c supra) in tetrahydrofuran (5 mL) at −78° C. and the reaction mixture was stirred at the same temperature for 2 hours then slowly allowed to warm up to −20° C. and stirred for 10 minutes. The reaction mixture was diluted with ethyl acetate (100 mL) and successively washed with saturated aqueous ammonium chloride solution (100 mL), water (50 mL) and brine (50 mL), dried over anhydrous sodium sulfate, filtered, and concentrated in vacuo. The residue was purified by flash column chromatography to give 3-(2,4-dichloro-pyrimidin-5-yl)-2-pyridin-3-yl-propionic acid ethyl ester as a brown oil. (Yield 1.10 g, 68.0%).

Example 10b 3-(2,4-Diphenylamino-pyrimidin-5-yl)-2-pyridin-3-yl-propionic acid ethyl ester

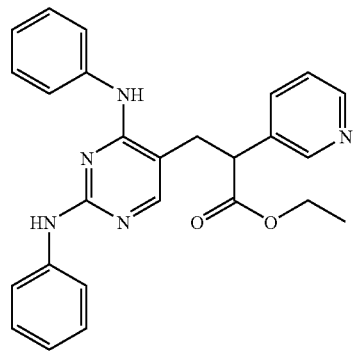

A mixture of 3-(2,4-dichloro-pyrimidin-5-yl)-2-pyridin-3-yl-propionic acid ethyl ester (326 mg, 1.0 mmol) (from Example 10a supra) and aniline (2.0 mL) (Aldrich) was heated at 120° C. for 1 hour. The reaction mixture was washed with hexanes (50 mL×3) and the supernatant was decanted off after each time. The residue was then dissolved in ethyl acetate (100 mL) and successively washed with saturated aqueous ammonium chloride solution (30 mL), water (30 mL) and brine (30 mL), dried over anhydrous sodium sulfate, filtered, and concentrated in vacuo. The crude product was purified by preparative thin layer chromatography to give 3-(2,4-diphenylamino-pyrimidin-5-yl)-2-pyridin-3-yl-propionic acid ethyl ester as a brown solid which was used in the next step without further purification. (Yield 60 mg, 13.7%).

Example 10c

8-Phenyl-2-phenylamino-6-pyridin-3-yl-5,8-dihydro-6H-pyrido[2,3-d]pyrimidin-7-one

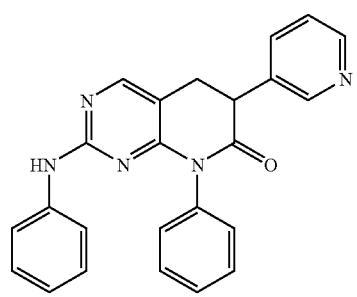

To a solution of 3-(2,4-diphenylamino-pyrimidin-5-yl)-2-pyridin-3-yl-propionic acid ethyl ester (60 mg, 0.36 mmol) (from Example 10b supra) was added 5% concentrated sulfuric acid in glacial acetic acid (3 mL) in one portion. The reaction mixture was heated at 120° C. for 3 hours. The reaction mixture was then diluted with ethyl acetate (100 mL) and quenched with 2 N aqueous sodium hydroxide solution. The organic layer was separated and successively washed with water (30 mL) and brine (30 mL), dried over anhydrous sodium sulfate, filtered, and concentrated in vacuo to give the crude product which was crystallized from ethyl acetate-hexanes to give 8-phenyl-2-phenylamino-6-pyridin-3-yl-5,8-dihydro-6H-pyrido[2,3-d]pyrimidin-7-one as a white solid. (Yield 37.3 mg, 69.3%).

HRMS m/z Calcd for $C_{24}H_{19}N_5O$ (M+): 393.1590. Found: 393.1586.

Example 11a 3-(2,4-Dichloro-pyrimidin-5-yl)-2-(3,4-dimethoxy-phenyl)-propionic acid ethyl ester

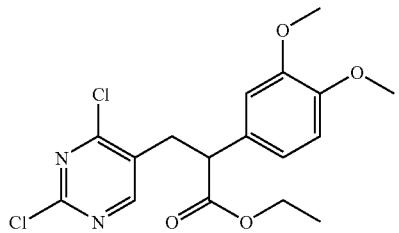

To a solution of N-isopropylcyclohexylamine (720 mg, 5.0 mmol) (Aldrich) in dry tetrahydrofuran (10 mL) was added n-butyllithium (2.5 M in hexanes, 2.0 mL, 5.0 mmol) (Aldrich) at −78° C. under argon. After 30 minutes, a solution of 3,4-dimethoxyphenylacetic acid ethyl ester (1.12 g, 5.0 mmol) (Lancaster) in tetrahydrofuran (3 mL) was added by injection via a syringe and the reaction mixture was stirred at −78° C. for another 30 minutes. To the reaction mixture was added a solution of 2,4-dichloro-5-iodomethyl-pyrimidine (722.5 mg, 2.5 mmol) (from Example 1c supra) in tetrahydrofuran (3 mL) at −78° C. and the reaction mixture was stirred at the same temperature for 1 hour then slowly allowed to warm up to −30° C. and stirred for 10 minutes. After cooling the reaction mixture was diluted with ethyl acetate (100 mL) and successively washed with saturated aqueous ammonium chloride solution (50 mL), water (30 mL) and brine (30 mL), dried over anhydrous sodium sulfate, filtered, and concentrated in vacuo. The residue was then purified by flash column chromatography to give 3-(2,4-dichloro-pyrimidin-5-yl)-2-(3,4-dimethoxy-phenyl)-propionic acid ethyl ester. (Yield 440 mg, 46.0%).

Example 11b 3-(2,4-Diphenylamino-pyrimidin-5-yl)-2-(3,4-dimethoxy-phenyl)-propionic acid ethyl ester

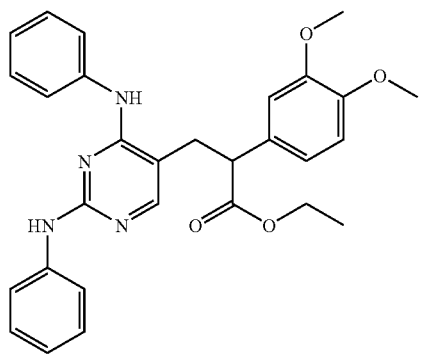

A mixture of 3-(2,4-dichloro-pyrimidin-5-yl)-2-(3,4-dimethoxy-phenyl)-propionic acid ethyl ester (440 mg, 1.1 mmol) (from Example 11a supra) and aniline (2.0 mL) (Aldrich) was heated at 110° C. for 2 hours. The reaction mixture was washed with hexanes (50 mL×3) and the supernatant was decanted off after each time. The residue was then dissolved in ethyl acetate (100 mL) and successively washed with saturated aqueous ammonium chloride solution (30 mL), water (30 mL) and brine (30 mL), dried over anhydrous sodium sulfate, filtered, and concentrated in vacuo. The residue was then purified by flash column chromatography to give the crude 3-(2,4-diphenylamino-pyrimidin-5-yl)-2-(3,4-dimethoxy-phenyl)-propionic acid ethyl ester as an off-white solid. (Yield 470 mg, 86%).

Example 11c 6-(3,4-Dimethoxy-phenyl)-8-phenyl-2-phenylamino-5,8-dihydro-6H-pyrido[2,3-d]pyrimidin-7-one

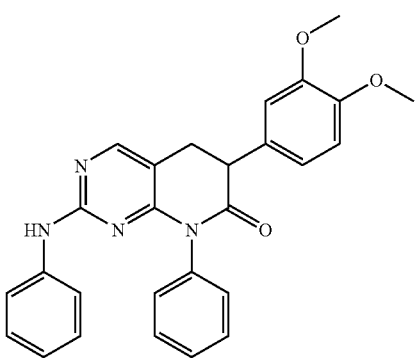

To a solution of 3-(2,4-diphenylamino-pyrimidin-5-yl)-2-(3,4-dimethoxy-phenyl)-propionic acid ethyl ester (470 mg, 0.94 mmol) (from Example 11b supra) in glacial acetic acid (3 mL) was added concentrated sulfuric acid (0.1 mL) in one portion. The reaction mixture was heated at 80° C. overnight. After cooling, the reaction mixture was diluted with ethyl acetate (50 mL) and quenched with 2 N aqueous sodium hydroxide solution. The organic layer was separated and successively washed with water (10 mL) and brine (10 mL), dried over anhydrous sodium sulfate, filtered, and concentrated in vacuo to give the crude product which was crystallized from ethyl acetate-hexanes to give 6-(3,4-dimethoxy-phenyl)-8-phenyl-2-phenylamino-5,8-dihydro-6H-pyrido[2,3-d]pyrimidin-7-one as a light brown solid. (Yield 335 mg, 78.8%).

HRMS m/z Calcd for $C_{27}H_{24}N_4O_3$ (M+): 452.1848. Found: 452.1844.

Example 12a 3-(4–Chloro-2-phenylamino-pyrimidin-5-yl)-2-(4-methoxy-phenyl)-propionic acid methyl ester To a solution of 3-(2,4-dichloro-pyrimidin-5-yl)-2-(4-methoxy-phenyl)-propionic acid methyl ester (341 mg, 1.0 mmol) (from Example 1d supra) in n-butanol (10 mL) was added aniline (200 mg, 2.15 mmol) (Aldrich) followed by N,N-diisopropylethylamine (258 mg, 2.0 mmol) (Aldrich) and the reaction mixture was heated at 100° C. for 12 hours. After cooling, the reaction mixture was diluted with ethyl acetate (100 mL) and successively washed with saturated aqueous ammonium chloride solution (30 mL), water (30 mL) and brine (30 mL), dried over anhydrous sodium sulfate, filtered, and concentrated in vacuo. The crude product was purified by flash column chromatography (silica gel) to give 3-(4-chloro-2-phenylamino-pyrimidin-5-yl)-2-(4-methoxy-phenyl)-propionic acid methyl ester. (Yield 45.1 mg, 11.3%).

Example 12b 3-(2–Chloro-4-phenylamino-pyrimidin-5-yl)-2-(4-methoxy-phenyl)-propionic acid methyl ester

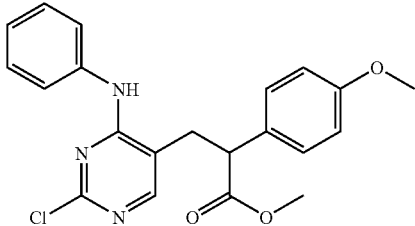

From the above reaction mixture (from Example 12a supra) flash column chromatography gave a second product 3-(2-chloro-4-phenylamino-pyrimidin-5-yl)-2-(4-methoxy-phenyl)-propionic acid methyl ester as an off-white amorphous solid. (Yield 310 mg, 77.9%).

Example 12c

3-[2-(6-Methoxy-pyridin-3-ylamino)-4-phenylamino-pyrimidin-5-yl]-2-(4-methoxy-phenyl)-propionic acid methyl ester

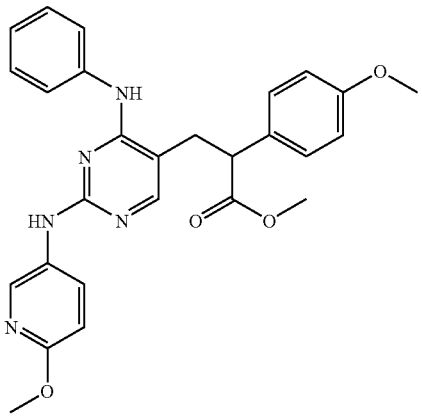

A mixture of 3-(2-chloro-4-phenylamino-pyrimidin-5-yl)-2-(4-methoxy-phenyl)-propionic acid methyl ester (40 mg, 0.1 mmol) (from Example 12b supra) and 5-amino-2-methoxypyridine (37.2 mg, 0.3 mmol) (Aldrich) was heated at 110° C. for 4 hours. After cooling, the reaction mixture was diluted with ethyl acetate (50 mL) and successively washed with saturated aqueous ammonium chloride solution (10 mL), water (10 mL) and brine (10 mL), dried over anhydrous sodium sulfate, filtered, and concentrated in vacuo to give crude 3-[2-(6-methoxy-pyridin-3-ylamino)-4-phenylamino-pyrimidin-5-yl]-2-(4-methoxy-phenyl)-propionic acid methyl ester as a dark-red solid which was used in the next step without further purification. (Yield 47.1 mg, 96.8%).

Example 12d 6-(4-Methoxy-phenyl)-2-(6-methoxy-pyridin-3-ylamino)-8-phenyl-5,8-dihydro-6H-pyrido[2,3-d]pyrimidine-7-one

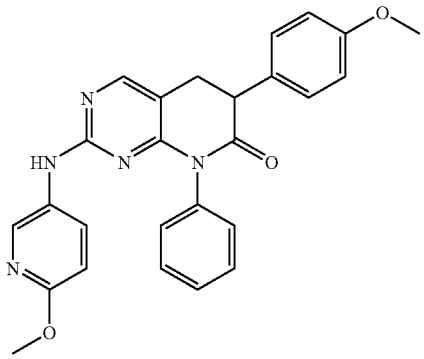

To a solution of 3-[2-(6-methoxy-pyridin-3-ylamino)-4-phenylamino-pyrimidin-5-yl]-2-(4-methoxy-phenyl)-propionic acid methyl ester (45.0 mg, 0.09 mmol) (from Example 12c supra) in glacial acetic acid (1 mL) was added concentrated sulfuric acid (0.1 mL) in one portion. After heating at 80° C. for 3 hours, the reaction mixture was diluted with ethyl acetate (50 mL) and quenched with 2 N aqueous sodium hydroxide solution. The organic layer was separated and successively washed with water (10 mL) and brine (10 mL), dried over anhydrous sodium sulfate, filtered, and concentrated in vacuo to give the crude product. The crude product was purified by preparative thin layer chromatography to give 6-(4-methoxy-phenyl)-2-(6-methoxy-pyridin-3-ylamino)-8-phenyl-5,8-dihydro-6H-pyrido[2,3-d]pyrimidine-7-one as brown powder. (Yield 5.2 mg, 12.4%).

HRMS m/z Calcd for $C_{26}H_{23}N_5O_3$ [(M+H)$^+$]: 454.1874. Found: 454.1878.

Example 13a 3-(2-Phenylamino-4-isobutylamino-pyrimidin-5-yl)-2-(4-methoxy-phenyl)-propionic acid methyl ester

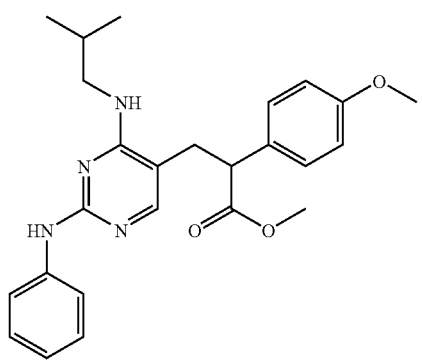

and

Example 13b

8-Isobutyl-6-(4-methoxy-phenyl)-2-phenylamino-5,8-dihydro-6H-pyrido[2,3-d]pyrimidine-7-one

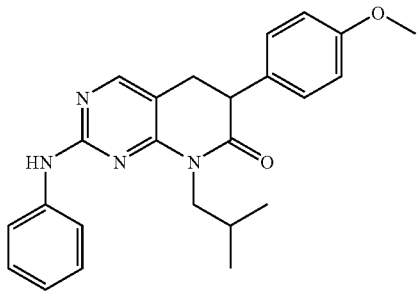

A mixture of 3-(4-chloro-2-phenylamino-pyrimidin-5-yl)-2-(4-methoxy-phenyl)-propionic acid methyl ester (40 mg, 0.1 mmol) (from Example 12a supra) and isobutylamine (2.0 mL) (Aldrich) was heated at reflux for 3 hours. The reaction mixture was concentrated in vacuo and purified by preparative thin layer chromatography to give 8-isobutyl-6-(4-methoxy-phenyl)-2-phenylamino-5,8-dihydro-6H-pyrido[2,3-d]pyrimidine-7-one; (Yield 4.6 mg, 11.4%); and 3-(2-phenylamino-4-isobutylamino-pyrimidin-5-yl)-2-(4-methoxy-phenyl)-propionic acid methyl ester. (Yield 18.2 mg, 41.9%).

To the solution of 3-(2-phenylamino-4-isobutylamino-pyrimidin-5-yl)-2-(4-methoxy-phenyl)-propionic acid methyl ester (17.1 mg, 0.04 mmol) in glacial acetic acid (1 mL) was added concentrated sulfuric acid (0.1 mL) in one portion. The reaction mixture was heated at 85° C. overnight. After cooling, the reaction mixture was diluted with ethyl acetate (50 mL) and quenched with 2 N aqueous sodium hydroxide solution. The organic layer was separated and successively washed with water (10 mL) and brine (10 mL), dried over anhydrous sodium sulfate, filtered, and concentrated in vacuo to give 8-isobutyl-6-(4-methoxy-phenyl)-2-phenylamino-5,8-dihydro-6H-pyrido[2,3-d]pyrimidine-7-one as a brown solid. (14.3 mg, 90.5%). HRMS m/z Calcd for $C_{24}H_{26}N_4O_2$ $[(M+H)^+]$: 403.2129. Found: 403.2131.

Example 14a 3-(2-Phenylamino-4-cyclopropylmethylamino-pyrimidin-5-yl)-2-(4-methoxy-phenyl)-propionic acid methyl ester

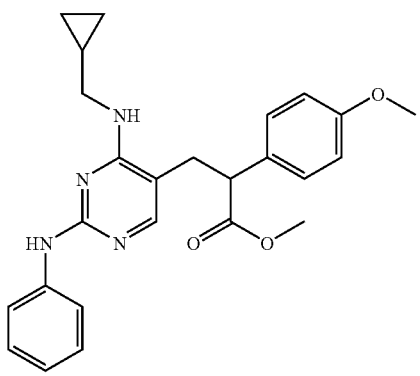

A mixture of 3-(4-chloro-2-phenylamino-pyrimidin-5-yl)-2-(4-methoxy-phenyl)-propionic acid methyl ester (45 mg, 0.11 mmol) (from Example 12a supra) and cyclopropylmethylamine (1.0 mL) (Lancaster) was stirred at room temperature for 24 hours. The reaction mixture was then diluted with ethyl acetate (50 mL) and successively washed with water (10 mL) and brine (10 mL), dried over anhydrous sodium sulfate, filtered, and concentrated in vacuo to give the crude 3-(2-phenylamino-4-cyclopropylmethylamino-pyrimidin-5-yl)-2-(4-methoxy-phenyl)-propionic acid methyl ester which was used in the next step without further purification. (Yield 51.3 mg).

Example 14b

8-Cyclopropylmethyl-6-(4-methoxy-phenyl)-2-phenylamino-5,8-dihydro-6H-pyrido[2,3-d]pyrimidine-7-one

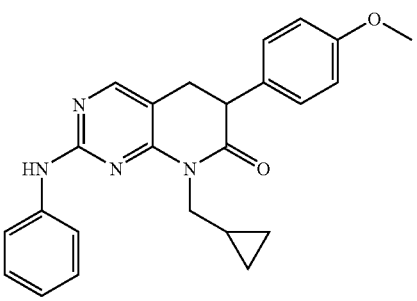

To a solution of crude 3-(2-phenylamino-4-cyclopropylmethylamino-pyrimidin-5-yl)-2-(4-methoxy-phenyl)-propionic acid methyl ester (51.3 mg) (from Example 14a supra) in glacial acetic acid (1 mL) was added concentrated sulfuric acid (0.1 mL) in one portion. The reaction mixture was heated at 85° C. for 3 hours. The reaction mixture was cooled, diluted with ethyl acetate (50 mL) and quenched with 2 N aqueous sodium hydroxide solution. The organic layer was separated and successively washed with water (10 mL) and brine (10 mL), dried over anhydrous sodium sulfate, filtered, and concentrated in vacuo. The residue was purified by preparative thin layer chromatography to give 8-cyclopropylmethyl-6-(4-methoxy-phenyl)-2-phenylamino-5,8-dihydro-6H-pyrido[2,3-d]pyrimidine-7-one as a light yellow amorphous solid. (Yield 6.7 mg, 14.8%, 2 steps).

HRMS m/z Calcd for $C_{24}H_{24}N_4O_2$ $[(M+H)^+]$: 401.1972. Found: 401.1973.

Antiproliferative Activity

The antiproliferative activity of the compounds of the invention is demonstrated below in Examples 15 and 16. These activities indicate that the compounds of the present invention are useful in treating cancer, in particular solid tumors such as breast and colon tumors.

Example 15

Kinase Assays

To determine inhibition of KDR, FGFR, EGFR, and PDGFR activity, kinase assays were conducted using an HTRF (Homogeneous Time Resolved Fluorescence) assay. This assay is described in A. J. Kolb et. al., Drug Discovery Today, 1998, 3(7), p 333.

Prior to kinase reaction, recombinant EEE-tagged KDR was activated in the presence of activation buffer (50 mM HEPES, pH 7.4, 1 mM DTT, 10% glycerol, 150 mM NaCl, 0.1 mM EDTA, 26 mM $MgCl_2$, and 4 mM ATP). The enzyme was incubated at 4° C. for 1 hour.

Kinase activity assays were performed in 96-well polypropylene plates (Falcon) with a total volume of 90 μL in each well. Each well contained 1 μM KDR substrate (Biotin-EEEEYFELVAKKKK), 1 nM activated KDR, and a test compound with one of 8 assay concentrations ranging from 100 μM to 128 pM (1:5 serial dilution). The kinase activity assay was done in the presence of 100 mM HEPES, pH 7.4, 1 mM DTT, 0.1 mM $Na_2VO_4$, 25 mM $MgCl_2$, 50 mM NaCl (from KDR stock solution), 1% DMSO (from compound), 0.3 mM ATP (at $K_m$ concentration) and 0.02% BSA. The reaction was incubated at 37° C. for 30 minutes. To stop the KDR reaction, 72 μL of reaction mixture was transferred into a STOP plate containing 18 μL of revelation buffer (20 mM EDTA, 50 mM HEPES, pH 7.4, 0.02% BSA, 10 nM Eu-labelled anti-pY antibody (final conc. 2 nM), and 100 nM streptavidin (final conc. 20 nM)). After mixing, 35 μL of solution was transferred into duplicate wells of a 384-well black plate (Costar), and read at 615/665 nm on a Wallac Victor 5 reader.

FGFR, EGFR, and PDGFR activity assays were carried out as described above for the KDR activity assay with the following differences. GST-tagged FGFR enzyme was activated at room temperature for 1 hour in the following activation buffer: 100 mM HEPES, pH 7.4, 50 mM NaCl, 20 mM $MgCl_2$, and 4 mM ATP. The kinase activity assay was performed with 1 μM substrate (Biotin-EEEEYFELV), 1.5 nM activated FGFR, and test compound in the presence of 100 mM HEPES, 1 mM DTT, 0.4 mM $MgCl_2$, 0.4 mM $MnCl_2$, 50 mM NaCl, 1% DMSO, 10 μM ATP ($K_m$=8.5 μM for FGFR), 0.1 mM $Na_2VO_4$, and 0.02% BSA, in a total volume of 90 μL. The rest of the assay was performed in the same manner as KDR assay.

The EGFR kinase activity assay was performed with 1 μM substrate (Biotin-EEEEYFELV), 1.5 nM EGFR, test compounds, 100 mM HEPES, pH 7.4, 1 mM DTT, 5 mM $MgCl_2$, 2 mM $MnCl_2$, 1% DMSO, 0.5 μM ATP ($K_m$ for EGFR), 0.1 mM $Na_2VO_4$, and 0.02% BSA. The rest of the assay was performed in the same manner as the KDR assay.

The PDGFR kinase activity assay was performed with 1 μM substrate (Biotin-EEEEYFELV), 1.0 nM PDGFR, test compounds, 100 mM HEPES, pH 7.4, 1 mM DTT, 5 mM $MgCl_2$, 2 mM $MnCl_2$, 1% DMSO, 2.3 μM ATP ($K_m$ for PDGFR), 0.1 mM $Na_2VO_4$, and 0.02% BSA. The rest of the assay was performed in the same manner as the KDR assay.

Compound $IC_{50}$ values were determined from duplicate sets of data, and calculated by using Excel and fitting data to equation $Y=[(a-b)/\{1+(X/c)^d\}]+b$, where a and b are enzyme activity in the presence of no test inhibitor compound and an infinite amount of inhibitor test compound, respectively, c is the $IC_{50}$ and d is the hill constant of the compound response. The $IC_{50}$ value is the concentration of test compound that reduces by 50% the enzyme activity under the test conditions described.

The results of the foregoing in vitro experiments, including $IC_{50}$ values, are set forth in Table 1 below.

TABLE 1

| | $IC_{50}$ of enzyme inhibition | | | |
|---|---|---|---|---|
| Example | KDR | FGFR | EGFR | PDGFR |
| | | $IC_{50}$ (μM) | | |
| 1f | <10 | <10 | <10 | <10 |
| 2c | <10 | <10 | <10 | <10 |
| 3d | <10 | <10 | <10 | <10 |
| 4c | <10 | <10 | <10 | <10 |
| 5c | <10 | <10 | <10 | <10 |
| 6c | <10 | <10 | <10 | <10 |
| 7c | <10 | <10 | <10 | <10 |
| 8d | >10 | >10 | >10 | <10 |
| 9c | <10 | >10 | <10 | >10 |
| 10c | <10 | <10 | <10 | <10 |
| 11c | <10 | <10 | >10 | <10 |
| 12d | <10 | <10 | <10 | <10 |
| 13b | <10 | <10 | <10 | <10 |
| 14b | <10 | <10 | <10 | <10 |

Example 16

VEGF and FGF-Stimulated HUVEC Proliferation Assays

The antiproliferative activity of test-compounds of this invention in cell-based assays was evaluated by BrdU assay using the BrdU kit (Roche Biochemicals 1-647-229). Human umbilical vein endothelial cells (Clonetics CC-2519) were cultured in EGM-2 (Clonetics CC-3162) medium and seeded at 10000 cells per well in a volume of 200 μL of EGM-2 (Clonetics CC-3162) media in a 96-well flat bottom plates (Costar 3595) overnight. After 24 hours of growth at 37° C. with 5% $CO_2$, the incubation media was removed slowly by aspiration and the content of each well was washed with 300 μL pre-warmed EBM-2 (Clonetics CC-3156) containing 50 μg per mL of gentamycin and 50 ng per mL of amphotercin-B (Clonetics CC-4083). Subsequently, the remaining media was again aspirated and replaced with 160 μL per well of serum starvation media (EBM-2 supplemented with 1% heat inactivated FBS (Clonetics CC-4102), 50 μg per mL gentamycin and 50 ng per mL of amphotercin-B (Clonetics CC-4083), 10 units per mL of Wyeth-Ayerst heparin (NDC0641-0391-25), and 2 mM L-glutamine (GIBCO 25030-081). After serum starving the cells for 24 hours, 20 μL of test compound at 10x test concentration in serum starvation medium with 2.5% DMSO was added to the appropriate wells. The control wells contained 20 μL of serum starvation medium with 2.5% DMSO. Plates were returned to the incubator for 2 hours. After pre-incubating the cells with the test compounds for 2 hours, 20 μL of growth factors at 10x assay concentration diluted in serum starvation media, FGF at 50 ng per mL, or VEGF (R&D systems 293-VE) at 200 ng per mL were added. The final concentration of FGF in the assay was 5 ng per mL. and the final concentration of VEGF in the assays was 20 ng per mL. The growth factor free control wells had 20 μL per well of serum starvation media with the same amount of BSA as the wells with growth factors. The plates were returned to the incubator for an additional 22 hours.

BrdU ELISA

After 24 hour exposure to the test compounds, the cells were labeled with BrdU (Roche Biochemicals 1-647-229), by adding 20 μL per well of BrdU labeling reagent that has been diluted (1:100) in serum starvation medium. The plates were then returned to the incubator for 4 hours. The labeling medium was removed by draining the medium onto paper towels. The cells were fixed and DNA denatured by adding 200 μL of fixation/denaturation solution to each well and incubating at room temperature for 45 minutes. The fixation/denaturation solution was drained onto paper towels and to each well was added 100 μL of anti-BrdU-POD and the wells were incubated for 2 hours at room temperature. The antibody solution was removed and the wells were each washed 3–4 times with 300 μL PBS. 100 μL of the TMB substrate solution was added to each well and the wells were incubated at room temperature for 5–8 minutes. The reaction was then stopped by adding 100 μL per well of 1 M phosphoric acid. The plates were read at 450 nm with reference wavelength of 650 nm. The percent inhibition for each test compound was calculated by subtracting the absorbency of the blank (no cells) wells from all wells, then subtracting the division of the average absorbency of each test duplicate by the average of the controls from 1. The final product was then multiplied by 100 (% of inhibition=(1-average absorbency of test duplicate/average of control) 100). The $IC_{50}$ value is the concentration of test compound that inhibits by 50% BrdU labeling, and is a measure of inhibition of cell proliferation. The $IC_{50}$ is determined from the linear regression of a plot of the logarithm of the concentration versus percent inhibition. The $IC_{50}$ values are shown in Table 2 below.

TABLE 2

$IC_{50}$ of VEGF and FGF-Stimulated HUVEC Proliferation Assays

| Example | HUVEC/VEFG | HUVEC/bFGFR |
|---|---|---|
| | $IC_{50}$ (μM) | |
| 2c | <10 | <10 |
| 3d | <10 | <10 |

Example 17

Tablet Formulation

| Item | Ingredients | Mg/Tablet | | | | | |
|---|---|---|---|---|---|---|---|
| 1 | Compound A* | 5 | 25 | 100 | 250 | 500 | 750 |
| 2 | Anhydrous Lactose | 103 | 83 | 35 | 19 | 38 | 57 |
| 3 | Croscarmellose Sodium | 6 | 6 | 8 | 16 | 32 | 48 |
| 4 | Povidone K30 | 5 | 5 | 6 | 12 | 24 | 36 |
| 5 | Magnesium Stearate | 1 | 1 | 1 | 3 | 6 | 9 |
| | Total Weight | 120 | 120 | 150 | 300 | 600 | 900 |

*Compound A represents a compound or the invention.

Manufacturing Procedure:

Mix Items 1, 2 and 3 in a suitable mixer for 15 minutes.

Granulate the powder mix from Step 1 with 20% Povidone K30 Solution (Item 4).

Dry the granulation from Step 2 at 50° C.

Pass the granulation from Step 3 through a suitable milling equipment.

Add the Item 5 to the milled granulation Step 4 and mix for 3 minutes.

Compress the granulation from Step 5 on a suitable press.

Example 18

Capsule Formulation

| Item | Ingredients | mg/Capsule | | | | |
|---|---|---|---|---|---|---|
| 1 | Compound A* | 5 | 25 | 100 | 250 | 500 |
| 2 | Anhydrous Lactose | 159 | 123 | 148 | — | — |
| 3 | Corn Starch | 25 | 35 | 40 | 35 | 70 |
| 4 | Talc | 10 | 15 | 10 | 12 | 24 |
| 5 | Magnesium Stearate | 1 | 2 | 2 | 3 | 6 |
| | Total Fill Weight | 200 | 200 | 300 | 300 | 600 |

*Compound A represents a compound of the invention.

Manufacturing Procedure:

Mix Items 1, 2 and 3 in a suitable mixer for 15 minutes.

Add Items 4 & 5 and mix for 3 minutes.

Fill into a suitable capsule.

Example 19

Injection Solution/Emulsion Preparation

| Item | Ingredient | mg/mL |
|---|---|---|
| 1 | Compound A* | 1 mg |
| 2 | PEG 400 | 10–50 mg |
| 3 | Lecithin | 20–50 mg |
| 4 | Soy Oil | 1–5 mg |
| 5 | Glycerol | 8–12 mg |
| 6 | Water q.s. | 1 mL |

*Compound A represents a compound of the invention.

Manufacturing Procedure:

Dissolve item 1 in item 2.

Add items 3, 4 and 5 to item 6 and mix until dispersed, then homogenize.

Add the solution from step 1 to the mixture from step 2 and homogenize until the dispersion is translucent.

Sterile filter through a 0.2 μm filter and fill into vials.

Example 20

Injection Solution/Emulsion Preparation

| Item | Ingredient | mg/mL |
|---|---|---|
| 1 | Compound A* | 1 mg |
| 2 | Glycofurol | 10–50 mg |
| 3 | Lecithin | 20–50 mg |
| 4 | Soy Oil | 1–5 mg |
| 5 | Glycerol | 8–12 mg |
| 6 | Water | q.s. 1 mL |

*Compound A represents a compound of the invention.

Manufacturing Procedure:

Dissolve item 1 in item 2.

Add items 3, 4 and 5 to item 6 and mix until dispersed, then homogenize.

Add the solution from step 1 to the mixture from step 2 and homogenize until the dispersion is translucent.

Sterile filter through a 0.2 μm filter and fill into vials.

While the invention has been illustrated by reference to specific and preferred embodiments, those skilled in the art will understand that variations and modifications may be made through routine experimentation and practice of the invention. Thus, the invention is intended not to be limited by the foregoing description, but to be defined by the appended claims and their equivalents.

What is claimed is:

1. A compound of formula

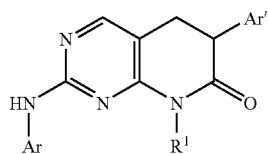

I or a pharmaceutical acceptable salt thereof, wherein

Ar and Ar' are independently selected from the group consisting of aryl, substituted aryl, heteroaryl and substituted heteroaryl, with the proviso that for Ar, the heteroaryl is not 2-pyridyl and substituted heteroaryl is not substituted 2-pyridyl;

$R^1$ is selected from the group consisting of

H;

$C_{1-10}$ alkyl;

$C_{1-10}$ alkyl independently substituted by up to three groups selected from aryl, heteroaryl, heterocycle, cycloalkyl, $NR^8R^9$, $OR^{10}$, $SR^{10}$, halogen, $COR^{11}$, $CO_2R^{11}$, $CONR^{11}R^{12}$, $SO_2NR^{11}R^{12}$, $SOR^{11}$, $SO_2R^{11}$, CN and $NO_2$, wherein the aryl, heteroaryl, heterocycle and cycloalkyl groups may each independently be substituted by up to three groups selected from $NR^8R^9$, $OR^{10}$, $SR^{10}$, halogen, $COR^{11}$, $CO_2R^{11}$, $CONR^{11}R^{12}$, $SO_2NR^{11}R^{12}$, $SOR^{11}$, $SO_2R^{11}$, CN and $NO_2$;

aryl;

aryl independently substituted by up to three groups selected from lower alkyl, $NR^8R^9$, $OR^{10}$, $SR^{10}$, halogen, $COR^{11}$, $CO_2R^{11}$, $CONR^{11}R^{12}$, $SO_2NR^{11}R^{12}$, $SOR^{11}$, $SO_2R^{11}$, CN and $NO_2$;

heteroaryl;

heteroaryl independently substituted by up to three groups selected from lower alkyl, $NR^8R^9$, $OR^{10}$, $SR^{10}$, halogen, $COR^{11}$, $CO_2R^{11}$, $CONR^{11}R^{12}$, $SO_2NR^{11}R^{12}$, $SOR^{11}$, $SO_2R^{11}$, CN and $NO_2$;

heterocycle;

heterocycle independently substituted by up to three groups selected from lower alkyl, $NR^8R^9$, $OR^{10}$, $SR^{10}$, halogen, $COR^{11}$, $CO_2R^{11}$, $CONR^{11}R^{12}$, $SO_2NR^{11}R^{12}$, $SOR^{11}$, $SO_2R^{11}$, CN and $NO_2$;

$C_{3-10}$ cycloalkyl;

$C_{3-10}$ cycloalkyl independently substituted by up to three groups selected from lower alkyl, substituted lower alkyl, $NR^8R^9$, $OR^{10}$, $SR^{10}$, halogen, $COR^{11}$, $CO_2R^{11}$, $CONR^{11}R^{12}$, $SO_2NR^{11}R^{12}$, $SOR^{11}$, $SO_2R^{11}$, CN and $NO_2$;

$C_{2-10}$ alkenyl;

$C_{2-10}$ alkenyl independently substituted by up to three groups selected from cycloalkyl, substituted cycloalkyl, heterocyclyl, substituted heterocycloalkyl, $NR^8R^9$, $OR^{10}$, $SR^{10}$, halogen, $COR^{11}$, $CO_2R^{11}$, $CONR^{11}R^{12}$, $SO_2NR^{11}R^{12}$, $SOR^{11}$, $SO_2R^{11}$, CN and $NO_2$;

$C_{2-10}$ alkynyl; and $C_{2-10}$ alkynyl independently substituted by up to three groups selected from $NR^8R^9$, $OR^{10}$, $SR^{10}$, halogen, $COR^{11}$, $CO_2R^{11}$, $CONR^{11}R^{12}$, $SO_2NR^{11}R^{12}$, $SOR^{11}$, $SO_2R^{11}$, CN and $NO_2$; and wherein $R^8$, $R^9$ and $R^{10}$ are independently H or lower alkyl;

$R^{11}$ and $R^{12}$ are independently selected from the group consisting of

H;

unsubstituted lower alkyl;

lower alkyl substituted by hydroxy, alkoxy or $NR^{21}R^{22}$;

unsubstituted cycloalkyl;

cycloalkyl substituted by hydroxy, alkoxy, lower alkyl or $NR^{21}R^{22}$;

unsubstituted heterocycle;

heterocycle substituted by hydroxy, alkoxy, lower alkyl or $NR^{21}R^{22}$;

or alternatively $NR^{11}R^{12}$ forms a ring having 3 to 7 atoms, the ring having no or at least one additional heteroatoms, with the proviso that if the heteroatom is N, the heteroatom may be substituted by one or more substituents selected from the group consisting of lower alkyl, $OR^{13}$, $COR^{14}$, $CO_2R^{14}$, $CONR^{14}R^{15}$, $SO_2R^{14}$, and $SO_2NR^{14}R^{15}$;

$R^{13}$ is selected from the group consisting of

H;

$COR^{14}$;

$CONR^{14}R^{15}$;

unsubstituted lower alkyl;

lower alkyl substituted by hydroxy, alkoxy or $NR^{21}R^{22}$, unsubstituted cycloalkyl;

cycloalkyl substituted by hydroxy, alkoxy, lower alkyl or $NR^{21}R^{22}$, unsubstituted heterocycle; and heterocycle substituted by hydroxy, alkoxy, lower alkyl or $NR^{21}R^{22}$;

$R^{14}$ and $R^{15}$ are independently selected from the group consisting of

H;

unsubstituted lower alkyl;

lower alkyl substituted by hydroxy, alkoxy or $NR^{21}R^{22}$;

unsubstituted cycloalkyl;

cycloalkyl substituted by hydroxy, alkoxy, lower alkyl or $NR^{21}R^{22}$;

unsubstituted heterocycle;

heterocycle substituted by hydroxy, alkoxy, lower alkyl or $NR^{21}R^{22}$;

or alternatively $NR^{14}R^{15}$ forms a ring having 3 to 7 atoms, the ring having no or at least one hetero atoms, with the proviso that if the heteroatom is N, the heteroatom may be substituted by one or more substituents selected from the group consisting of lower alkyl, $OR^{23}$, $COR^{23}$, $CO_2R^{23}$, $CONR^{23}R^{24}$, $SO_2R^{23}$, $SO_2NR^{23}R^{24}$;

$R^{21}$ is selected from the group consisting of H, lower alkyl, $COR^{23}$ or $CO_2R^{23}$;

$R^{22}$, $R^{23}$ and $R^{24}$ are independently selected from the group consisting of H or lower alkyl, or alternatively $NR^{21}R^{22}$ or $NR^{23}R^{24}$ independently forms a ring having 3 to 7 atoms, the ring having no or at least one additional heteroatoms selected from the group consisting of N, O, or S, with the proviso that if the heteroatom is N, the heteroatom may be in the form of —NH or NR²⁵, and if the hetero atom is S, it may be in the form of $S(O)_m$ where m=0, 1 or 2; and R²⁵ is lower alkyl.

2. The compound of claim 1 wherein Ar is a substituted heteroaryl, with the proviso that the substituted heteroaryl is not 2-pyridyl.

3. The compound of claim 1 wherein Ar' is aryl, substituted aryl or heteroaryl.

4. The compound of claim 1 wherein R¹ is aryl, substituted aryl or heteroaryl.

5. A compound of formula

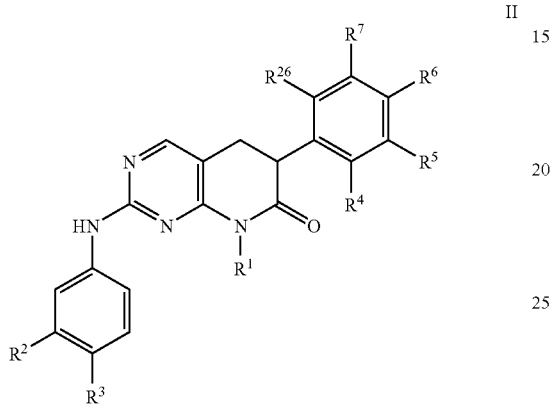

II or a pharmaceutically acceptable salt thereof, where

R¹ is selected from the group consisting of
H;
$C_{1-10}$ alkyl;
$C_{1-10}$ alkyl independently substituted by up to three groups selected from aryl, heteroaryl, heterocycle, cycloalkyl, NR⁸R⁹, OR¹⁰, SR¹⁰, halogen, COR¹¹, CO₂R¹¹, CONR¹¹R¹², SO₂NR¹¹R¹², SOR¹¹, SO₂R¹¹, CN and NO₂, wherein the aryl, heteroaryl, heterocycle and cycloalkyl groups may each independently be substituted by up to three groups selected from NR⁸R⁹, OR¹⁰, SR¹⁰, halogen, COR¹¹, CO₂R¹¹, CONR¹¹R¹², SO₂NR¹¹R¹², SOR¹¹, SO₂R¹¹, CN and NO₂;
aryl;
aryl independently substituted by up to three groups selected from lower alkyl, NR⁸R⁹, OR¹⁰, SR¹⁰, halogen, COR¹¹, CO₂R¹¹, CONR¹¹R¹², SO₂NR¹¹R¹², SOR¹¹, SO₂R¹¹, CN and NO₂;
heteroaryl;
heteroaryl independently substituted by up to three groups selected from lower alkyl, NR⁸R⁹, OR¹⁰, SR¹⁰, halogen, COR¹¹, CO₂R¹¹, CONR¹¹R¹², SO₂NR¹¹R¹², SOR¹¹, SO₂R¹¹, CN and NO₂;
heterocycle;
heterocycle independently substituted by up to three groups selected from lower alkyl, NR⁸R⁹, OR¹⁰, SR¹⁰, halogen, COR¹¹, CO₂R¹¹, CONR¹¹R¹², SO₂NR¹¹R¹², SOR¹¹, SO₂R¹¹, CN and NO₂;
$C_{3-10}$ cycloalkyl;
$C_{3-10}$ cycloalkyl independently substituted by up to three groups selected from lower alkyl, substituted lower alkyl, NR⁸R⁹, OR¹⁰, SR¹⁰, halogen, COR¹¹, CO₂R¹¹, CONR¹¹R¹², SO₂NR¹¹R¹², SOR¹¹, SO₂R¹¹, CN and NO₂;
$C_{2-10}$ alkenyl;
$C_{2-10}$ alkenyl independently substituted by up to three groups selected from cycloalkyl, substituted cycloalkyl, heterocyclyl, substituted heterocycloalkyl, NR⁸R⁹, OR¹⁰, SR¹⁰, halogen, COR¹¹, CO₂R¹¹, CONR¹¹R¹², SO₂NR¹¹R¹², SOR¹¹, SO₂R¹¹, CN and NO₂;
$C_{2-10}$ alkynyl; and
$C_{2-10}$ alkynyl independently substituted by up to three groups selected from NR⁸R⁹, OR¹⁰, SR¹⁰, halogen, COR¹¹, CO₂R¹¹, CONR¹¹R¹², SO₂NR¹¹R¹², SOR¹¹, SO₂R¹¹, CN and NO₂; and wherein R⁸, R⁹ and R¹⁰ are independently H or lower alkyl;

R² and R³ are independently selected from the group consisting of
NR¹¹R¹²;
OR¹³;
SR¹⁶;
halogen;
COR¹⁴;
CO₂R¹⁴;
CONR¹⁴R¹⁵;
SO₂NR¹⁴R¹⁵;
SO₂R¹⁴;
CN;
NO₂;
$(CH_2)_n$heteroaryl;
$(CH_2)_n$heterocycle;
$C_1$–$C_{10}$ alkyl;
$C_3$–$C_{10}$ cycloalkyl;
$C_2$–$C_{10}$ alkenyl;
$C_2$–$C_{10}$ alkynyl;
where n is 0, 1, 2, or 3 and the aryl, heteroaryl, heterocycle, alkyl, cycloalkyl, alkenyl, and alkynyl groups are unsubstituted or substituted by up to three groups selected from
NR¹¹R¹²;
OR¹³;
SR¹⁶;
halogen;
COR¹⁴;
CO₂R¹⁴;
CONR¹⁴R¹⁵;
SO₂NR¹⁴R¹⁵;
SO₂R¹⁴;
CN; and
NO₂;
or alternatively, R² and R³ together form a ring having 3 to 7 atoms fused to the phenyl ring that they are attached to, the ring having no or at least one additional heteroatoms, with the proviso that if the heteroatom is N, the heteroatom may be substituted by at least one substituent selected from the group consisting of
lower alkyl;
lower alkyl substituted by hydroxy, alkoxy or NR¹¹R¹²;
NR¹¹R¹²;
OR¹³;
SR¹⁶;
COR¹⁴;
CO₂R¹⁴;
CONR¹⁴R¹⁵;
SO₂NR¹⁴R¹⁵;
SO₂R¹⁴; and
CN;

$R^4$, $R^5$, $R^6$, $R^7$ and $R^{26}$ are independently selected from the group, with at least one being H, consisting of
H;
unsubstituted lower alkyl;
lower alkyl substituted by hydroxy, alkoxy or halogen;
$NR^{21}R^{22}$;
$OR^{23}$;
$SR^{23}$;
halogen;
$NO_2$;
$COR^{23}$;
$CO_2R^{23}$;
$CONR^{23}R^{24}$;
$SO_2NR^{23}R^{24}$;
$SO_2R^{23}$; and
CN;
$R^{11}$ and $R^{12}$ are independently selected from the group consisting of
H;
unsubstituted lower alkyl;
lower alkyl substituted by hydroxy, alkoxy or $NR^{21}R^{22}$;
unsubstituted cycloalkyl;
cycloalkyl substituted by hydroxy, alkoxy, lower alkyl or $NR^{21}R^{22}$;
unsubstituted heterocycle; and
heterocycle substituted by hydroxy, alkoxy, lower alkyl or $NR^{21}R^{22}$;
or alternatively $NR^{11}R^{12}$ forms a ring having 3 to 7 atoms, the ring having no or at least one additional heteroatoms, with the proviso that if the hetero atom is N, the heteroatom may be substituted by one or more substituents selected from the group consisting of lower alkyl, $COR^{14}$, $CO_2R^{14}$, $CONR^{14}R^{15}$, $SO_2R^{14}$, and $SO_2NR^{14}R^{15}$;
$R^{13}$ is selected from the group consisting of
H;
$COR^{14}$;
$CONR^{14}R^{15}$;
unsubstituted lower alkyl;
lower alkyl substituted by hydroxy, alkoxy or $NR^{21}R^{22}$;
unsubstituted cycloalkyl;
cycloalkyl substituted by hydroxy, alkoxy, lower alkyl or $NR^{21}R^{22}$;
unsubstituted heterocycle; and
heterocycle substituted by hydroxy, alkoxy, lower alkyl or $NR^{21}R^{22}$;
$R^{14}$ and $R^{15}$ are independently selected from the group consisting of
H;
unsubstituted lower alkyl;
lower alkyl substituted by hydroxy, alkoxy or $NR^{21}R^{22}$;
unsubstituted cycloalkyl;
cycloalkyl substituted by hydroxy, alkoxy, lower alkyl or $NR^{21}R^{22}$;
unsubstituted heterocycle; and
heterocycle substituted by hydroxy, alkoxy, lower alkyl or $NR^{21}R^{22}$, or alternatively $NR^{14}R^{15}$ forms a ring having 3 to 7 atoms, the ring having no or at least one additional heteroatoms, with the proviso that if the heteroatom is N, the heteroatom may be substituted by one or more substituents selected from the group consisting of one or more lower alkyl, $COR^{23}$, $CO_2R^{23}$, $CONR^{23}R^{24}$, $SO_2R^{23}$, $SO_2NR^{23}R^{24}$;
$R^{16}$ is selected from the group consisting of
unsubstituted lower alkyl;
lower alkyl substituted by hydroxy, alkoxy or $NR^{21}R^{22}$;
unsubstituted cycloalkyl;
cycloalkyl substituted by hydroxy, alkoxy, lower alkyl or $NR^{21}R^{22}$;
unsubstituted heterocycle; and
heterocycle substituted by hydroxy, alkoxy, lower alkyl or $NR^{21}R^{22}$;
$R^{21}$ is selected from the group consisting of H, lower alkyl, $COR^{23}$ or $CO_2R^{23}$;
$R^{22}$, $R^{23}$ and $R^{24}$ are independently selected from the group consisting of H or lower alkyl, or alternatively $NR^{21}R^{22}$ or $NR^{23}R^{24}$ independently forms a ring having 3 to 7 atoms, the ring having no or at least one additional heteroatom selected from the group consisting of N, O, and S, with the proviso that if the heteroatom is N, the heteroatom may be in the form of —NH or $NR^{25}$, and if the hetero atom is S, it may be in the form of $S(O)_m$ where m=0, 1 or 2; and
$R^{25}$ is lower alkyl.

6. The compound of claim 5 wherein $R^6$ is $OR^{23}$.

7. The compound of claim 5 wherein $R^4$ and $R^{26}$ are halogen.

8. The compound of claim 5 wherein $R^5$ and $R^7$ are $OR^{23}$.

9. The compound of claim 5 wherein $R^{26}$ is an unsubstituted lower alkyl.

10. The compound of claim 5 wherein $R^4$, $R^5$, $R^6$ and $R^{26}$ are H.

11. The compound of claim 5 wherein $R^5$ and $R^{26}$ are $OR^{22}$.

12. The compound of claim 5 wherein $R^{26}$ is $OR^{23}$.

13. The compound of claim 5 wherein $R^6$ and $R^7$ are $OR^{23}$.

14. The compound of claim 5 wherein $R^6$ is $OR^{23}$.

15. A compound selected from the group:
6-(4-Methoxy-phenyl)-8-phenyl-2-phenylamino-5,8-dihydro-6H-pyrido[2,3-d]pyrimidin-7-one (Example 1f);
6-(2,6-Dichloro-phenyl)-8-phenyl-2-phenylamino-5,8-dihydro-6H-pyrido[2,3-d]pyrimidin-7-one (Example 2c);
6-(3,5-Dimethoxy-phenyl)-8-phenyl-2-phenylamino-5,8-dihydro-6H-pyrido[2,3-d]pyrimidin-7-one (Example 3d);
8-Phenyl-2-phenylamino-6-O-tolyl-5,8-dihydro-6H-pyrido[2,3-d]pyrimidin-7-one (Example 4c);
6,8-Diphenyl-2-phenylamino-5,8-dihydro-6H-pyrido[2,3-d]pyrimidin-7-one (Example 5c);
6-(2,5-Dimethoxy-phenyl)-8-phenyl-2-phenylamino-5,8-dihydro-6H-pyrido[2,3-d]pyrimidin-7-one (Example 6c); and
6-(2-Methoxy-phenyl)-8-phenyl-2-phenylamino-5,8-dihydro-6H-pyrido[2,3-d]pyrimidin-7-one (Example 7c).

16. A compound selected from the group:
6-(3,5-Bis-trifluromethyl-phenyl)-8-phenyl-2-phenylamino-5,8-dihydro-6H-pyrido[2,3-d]pyrimidin-7-one (example 8d);
8-Phenyl-2-phenylamino-6-pyridin-4-yl-5,8-dihydro-6H-pyrido[2,3-d]pyrimidin-7-one (Example 9c);
8-Phenyl-2-phenylamino-6-pyridin-3-yl-5,8-dihydro-6H-pyrido[2,3-d]pyrimidin-7-one (Example 10c);
6-(3,4-Dimethoxy-phenyl)-8-phenyl-2-phenylamino-5,8-dihydro-6H-pyrido[2,3-d]pyrimidin-7-one (Example 11c);
6-(4-Methoxy-phenyl)-2-(6-methoxy-pyridin-3-ylamino)-8-phenyl-5,8-dihydro-6H-pyrido[2,3-d]pyrimidine-7-one (Example 12d);
8-Isobutyl-6-(4-methoxy-phenyl)-2-phenylamino-5,8-dihydro-6H-pyrido[2,3-d]pyrimidine-7-one (Example 13b); and 8-Cyclopropylmethyl-6-(4-methoxy-phenyl)-2-phenylamino-5,8-dihydro-6H-pyrido[2,3-d]pyrimidine-7-one (Example 14b).

17. A compound selected from the group:
3-(2,4-Dichloro-pyrimidin-5-yl)-2-(4-methoxy-phenyl)-propionic acid methyl ester (Example 1d);
3-(2,4-Diphenylamino-pyrimidin-5-yl)-2-(4-methoxy-phenyl)-propionic acid methyl ester (Example 1e);
2-(2,6-Dichloro-phenyl)-3-(2,4-dichloro-pyrimidin-5-yl)-propionic acid methyl ester (Example 2a);
3-(2,4-Diphenylamino-pyrimidin-5-yl)-2-(2,6-Dichloro-phenyl)-propionic acid methyl ester (Example 2b);
3-(2,4-Dichloro-pyrimidin-5-yl)-2-(3,5-dimethoxy-phenyl)-propionic acid methyl ester (Example 3b);
3-(2,4-Diphenylamino-pyrimidin-5-yl)-2-(3,5-dimethoxy-phenyl)-propionic acid methyl ester (Example 3c);
3-(2,4-Dichloro-pyrimidin-5-yl)-2-O-tolyl-propionic acid methyl ester (Example 4a);
3-(2,4-Diphenylamino-pyrimidin-5-yl)-2-O-tolyl-propionic acid methyl ester (Example 4b)
3-(2,4-Dichloro-pyrimidin-5-yl)-2-phenyl-propionic acid methyl ester (Example 5a); and
3-(2,4-Diphenylamino-pyrimidin-5-yl)-2-phenyl-propionic acid methyl ester (Example 5b).

18. A compound selected from the group:
3-(2,4-Dichloro-pyrimidin-5-yl)-2-(2,5-dimethoxy-phenyl)-propionic acid ethyl ester (Example 6a);
3-(2,4-Diphenylamino-pyrimidin-5-yl)-2-(2,5-dimethoxy-phenyl propionic acid ethyl ester (Example 6b);
3-(2,4-Dichloro-pyrimidin-5-yl)-2-(2-methoxy-phenyl)-propionic acid methyl ester (Example 7a);
3-(2,4-Diphenylamino-pyrimidin-5-yl)-2-(2-methoxy-phenyl) propionic acid ethyl ester (Example 7b);
2-(3,5-Bis-trifluoromethyl-phenyl)-3-(2,4-dichloro-pyrimidin-5-yl)-propionic acid methyl ester (Example 8b);
3-(2,4-Diphenylamino-pyrimidin-5-yl)-2-(3,5-bis-trifluoromethyl-phenyl)-propionic acid methyl ester (Example 8c);
3-(2,4-Dichloro-pyrimidin-5-yl)-2-pyridin-4-yl-propionic acid ethyl ester (Example 9a);
3-(2,4-Diphenylamino-pyrimidin-5-yl)-2-pyridin-4-yl-propionic acid ethyl ester (Example 9b);
3-(2,4-Dichloro-pyrimidin-5-yl)-2-pyridin-3-yl-propionic acid ethyl ester (Example 10a); and
3-(2,4-Diphenylamino-pyrimidin-5-yl)-2-pyridin-3-yl-propionic acid ethyl ester (Example 10b).

19. A compound selected from the group:
3-(2,4-Dichloro-pyrimidin-5-yl)-2-(3,4-dimethoxy-phenyl)-propionic acid ethyl ester (Example 11a);
3-(2,4-Diphenylamino-pyrimidin-5-yl)-2-(3,4-dimethoxy-phenyl)-propionic acid ethyl ester (Example 11b);
3-(4-Chloro-2-phenylamino-pyrimidin-5-yl)-2-(4-methoxy-phenyl)-propionic acid methyl ester (Example 12a);
3-(2-Chloro-4-phenylamino-pyrimidin-5-yl)-2-(4-methoxy-phenyl)-propionic acid methyl ester (Example 12b);
3-[2-(6-Methoxy-pyridin-3-ylamino)-4-phenylamino-pyrimidin-5-yl]-2-(4-methoxy-phenyl)-propionic acid methyl ester (Example 12c);
3-(2-Phenylamino-4-isobutylamino-pyrimidin-5-yl)-2-(4-methoxy-phenyl)-propionic acid methyl ester (Example 13a); and
3-(2-Phenylamino-4-cyclopropylmethylamino-pyrimidin-5-yl)-2-(4-methoxy-phenyl)-propionic acid methyl ester (Example 14a).

20. A pharmaceutical composition comprising a therapeutically effective amount of a compound of claim 1 and a pharmaceutically acceptable carrier or excipient.

21. A pharmaceutical composition comprising a therapeutically effective amount of a compound of claim 9 and a pharmaceutically acceptable carrier or excipient.

* * * * *